United States Patent [19]

Zimmerman

[11] Patent Number: 4,514,213
[45] Date of Patent: Apr. 30, 1985

[54] HERBICIDAL SULFONAMIDES

[75] Inventor: William T. Zimmerman, Landenberg, Pa.

[73] Assignee: E. I. Du Pont de Nemours and Company, Wilmington, Del.

[21] Appl. No.: 590,881

[22] Filed: Mar. 19, 1984

[51] Int. Cl.$^3$ ............... C07D 251/18; C07D 251/46; A01N 43/66; A01N 43/70
[52] U.S. Cl. ......................................... 71/93; 544/211; 544/212; 544/206; 544/207; 544/208; 544/209
[58] Field of Search .................... 71/93; 544/211, 212, 544/206, 207, 208, 209

[56] References Cited

U.S. PATENT DOCUMENTS 4,378,991 4/1983 Levitt .................................. 544/211
4,474,600 10/1984 Aya et al. ............................ 544/211

Primary Examiner—John M. Ford

[57] ABSTRACT

Novel benzenesulfonylurea compounds containing phenyl or phenoxy substituents such as 2-[[(4,6-dimethoxypyrimidin-2-yl)aminocarbonyl]aminosulfonyl]-4-phenylbenzoic acid, methyl ester, and 2-[[(4-methoxy-6-methyl-1,3,5-triazin-2-yl)aminocarbonyl]aminosulfonyl]-4-phenylbenzoic acid, methyl ester, herbicidal compositions containing these compounds, and their method of use as general or selective pre-emergent or post-emergent herbicides.

19 Claims, No Drawings

HERBICIDAL SULFONAMIDES

BACKGROUND OF THE INVENTION

Herbicidal benzenesulfonylurea compounds are disclosed in U.S. Pat. Nos. 4,127,405 and 4,169,719. Herbicidal benzenesulfonylureas disclosed in U.S. Pat. No. 4,378,991 contain ortho-phenyl or benzyl substituents such as South African Patent Application No. 826755 (priority date 9/16/81) teaches substituted phenylsulfonylureas such as wherein
X is O or a single bond;
Y and Z are independently halogen, $C_1$–$C_6$ alkyl, $C_1$–$C_6$ alkoxy or $NO_2$; and
R is substituted pyrimidine or triazine.

South African Patent Application No. 820465 (Japanese priority 1/26/81; EP-A-56,969, published 8/4/82) discloses herbicidal sulfonylureas such as wherein
R is substituted pyrimidine or triazine; and
n is 0 or 1.

Japanese Patent Application No. 8126872-A (priority date 1/22/82) teaches the ortho-phenyl and phenoxy sulfonylureas shown below.

wherein
X is O or a single bond;
Y is H or halogen;
$R_1$ is H, lower alkyl, etc. and
$R_2$ is a substituted pyrimidine or triazine.

SUMMARY OF THE INVENTION

This invention relates to novel compounds of Formula I, agriculturally suitable compositions containing them and their method of use as general or selective pre-emergent and post-emergent herbicides or as plant growth regulants.

wherein
E is O or a single bond;
$L_1$ is H, F, Cl, Br, $NO_2$, $CH_3$, $OCH_3$ or $CF_3$;
$L_2$ is H, F, Cl, Br, $CH_3$ or $OCH_3$;
R is H or $CH_3$;
$R_1$ is $CO_2R_2$, $S(O)_nR_3$, $SO_2NR_4R_5$, $SO_2N(OCH_3)CH_3$, $OSO_2R_6$, $WCF_3$, $WCHF_2$, $C_3$–$C_4$ alkenyloxy, $C_3$–$C_4$ alkynyloxy, $C_1$–$C_2$ alkyl substituted with $OCH_3$ or $OC_2H_5$, $CH_2CH_2Cl$, $CF_3$, $R_2$ is $C_1$–$C_3$ alkyl, $CH_2CH=CH_2$, $CH_2CH_2OCH_3$ or $CH_2CH_2Cl$;
$R_3$ is $C_1$–$C_3$ alkyl or $CH_2CH=CH_2$;
$R_4$ is H or $C_1$–$C_2$ alkyl;
$R_5$ is $C_1$–$C_2$ alkyl;
$R_6$ is $C_1$–$C_3$ alkyl, $CF_3$ or $N(CH_3)_2$;
W is O or S;
n is 0, 1 or 2;
A is

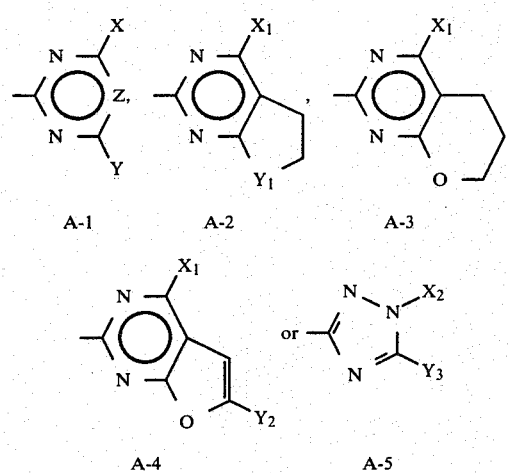

A-1   A-2   A-3

A-4   A-5

X is $CH_3$, $OCH_3$, $OCH_2CH_3$, Cl, F, Br, $OCF_2H$, $CH_2F$ $CH_2Cl$, $CH_2Br$ or $CF_3$;

Y is H, $CH_3$, $OCH_3$, $OCH_2CH_3$, $CH_2OCH_3$, $CH_2OCH_2CH_3$, $NH_2$, $NHCH_3$, $N(CH_3)_2$, $N(OCH_3)CH_3$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $OCH_2CH_2F$, $-CH(OCH_3)_2$,

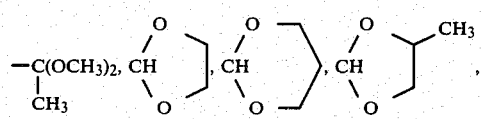

$CH(OCH_2CH_3)_2$ or

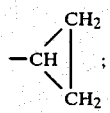

Z is CH or N;
$Y_1$ is $CH_2$ or O;
$X_1$ is $CH_3$, $OCH_3$, $OCH_2CH_3$ or $OCF_2H$;
$Y_2$ is H or $CH_3$;
$X_2$ is $CH_3$, $CH_2CH_3$ or $CH_2CF_3$;
$Y_3$ is $OCH_3$, $OCH_2CH_3$, $SCH_3$, $CH_3$ or $CH_2CH_3$; provided that when X is CL, F or Br, then Z is CH and Y is $OCH_3$, $OCH_2CH_3$, $NH_2$, $NHCH_3$, $N(CH_3)_2$ or $OCF_2H$.

Preferred for their higher herbicidal activity, greater plant growth regulant activity and/or more favorable ease of synthesis are:

(1) Compounds of Formula I where $R_1$ is in the 6-position and R is H;
(2) Compounds of Preferred 1 where A is A-1 and Y is $CH_3$, $C_2H_5$, $OCH_3$, $OC_2H_5$, $CH_2OCH_3$, $CH_2OC_2H_5$, $CF_3$, $OCH_2CF_3$ or $CH(OCH_3)_2$;
(3) Compounds of Preferred 2 where $L_2$ is H, $R_1$ is $CO_2R_2$, $SO_2R_3$, $SO_2NR_4R_5$ or $SO_2N(OCH_3)CH_3$ and $R_4$ is $C_1-C_2$ alkyl;
(4) Compounds of Preferred 3 where $L_1$ is H, Cl or $CH_3$, X is $CH_3$, $OCH_3$ or Cl and Y is $CH_3$, $C_2H_5$, $OCH_3$, $OC_2H_5$ or $CH_2OCH_3$;
(5) Compounds of Preferred 4 where E is a single bond and $L_1$ is H.

Specifically Preferred for their highest herbicidal activity, greatest plant growth regulant activity and/or most favorable ease of synthesis are:
2-[[(4,6-dimethoxypyrimidin-2-yl)aminocarbonyl-]aminosulfonyl]-4-phenylbenzoic acid, methyl ester, m.p. 190°-194° C.; and
2-[[(4-methoxy-6-methyl-1,3,5-triazin-2-yl)aminocarbonyl]aminosulfonyl]-4-phenylbenzoic acid, methyl ester, m.p. 198°-200° C.

DETAILED DESCRIPTION OF THE INVENTION

Synthesis

The compounds of Formula I may be prepared by reacting the appropriately substituted benzenesulfonyl isocyanate, II, with an appropriate aminoheterocycle, III, as shown in Equation 1.

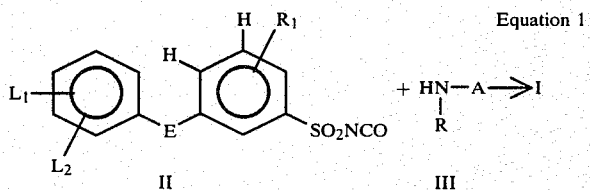

wherein A, E, R, $R_1$, $L_1$ and $L_2$ are as previously defined.

The reaction of Equation 1 can best be carried out in an inert aprotic solvent such as methylene chloride, tetrahydrofuran or acetonitrile at a temperature between 20° and 80° C. A catalytic amount of 1,4-diazabicyclo[2.2.2]octane (DABCO®) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, ethyl ether or methanol and filtration.

The benzenesulfonyl isocyanates of Formula II may be prepared as shown below in Equation 2, by phosgenation of the sulfonamide IV in the presence of butyl isocyanate. The sulfonyl isocyanates of Formula II may also be prepared, as shown in Equation 3, by phosgenation of the butylureas of Formula V.

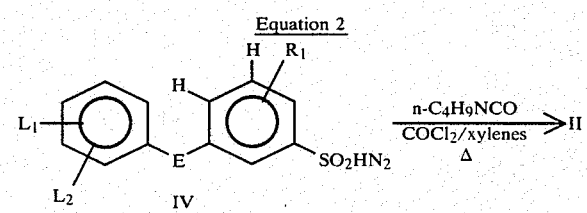

wherein E, $L_1$, $L_2$, and $R_1$ are as defined above.

The above reaction can be carried out by heating a mixture of the appropriate sulfonamide (IV), an alkyl isocyanate such as butyl isocyanate and a catalytic amount of a tertiary amine such as 1,4-diaza[2.2.2]bicyclooctane (DABCO®) in xylene, or other inert solvent of boiling point ≧135° to approximately 135° C. Phosgene can then be added to the mixture over a 1-6 hour period until an excess of phosgene is present as indicated by a drop in the boiling point to less than 130° C. The mixture is then cooled and filtered to remove a small amount of insoluble by-products. The solvent and the alkyl isocyanate can be distilled off in vacuo leaving a residue of the crude sulfonyl isocyanate, II, which can be used without further purification.

Equation 3

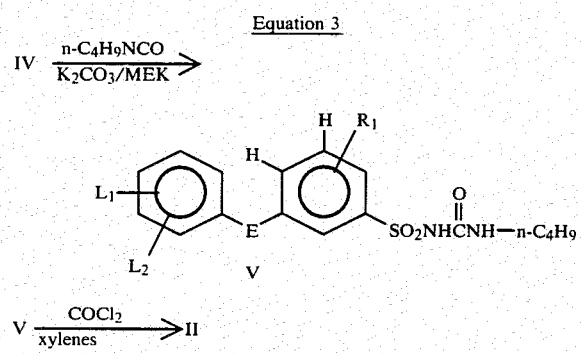

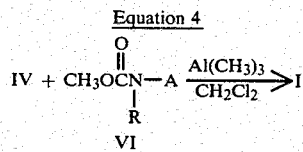

wherein $L_1$, $L_2$, E, and $R_1$ are as defined above.

The compounds of Formula V can be prepared by stirring a mixture of the sulfonamides, IV, anhydrous potassium carbonate, and n-butyl isocyanate in acetone or methyl ethyl ketone at 25°–80° C. until all of the sulfonamide has reacted. The products can be isolated by quenching in dilute mineral acid and recrystallizing the solid product. The compounds V are then treated with phosgene and a catalytic amount of DABCO ® in refluxing xylene or chlorobenzene in a manner analogous to that described in Equation 2.

Benzenesulfonyl isocyanates of Formula II may also be prepared according to the methods disclosed in German Offen. No. 3,132,944 in which a sulfonamide such as IV is treated with chlorosulfonyl isocyanate in an inert solvent such as chlorobenzene with a base catalyst such as DABCO ® at elevated temperature (e.g. 80° to 100° C. for 1 to 4 hours).

Alternatively, benzenesulfonylureas of Formula I, wherein $R_1$ is other than $CO_2R_2$, may be prepared by reacting an appropriately substituted benzenesulfonamide IV with an appropriate methyl heteroaryl carbamate VI in the presence of an equimolar amount of trimethylaluminum according to the procedure of Equation 4.

Equation 4

$$\text{IV} + \text{CH}_3\text{O} \overset{\overset{\text{O}}{\|}}{\text{C}} \text{N} - \text{A} \quad \underset{\text{CH}_2\text{Cl}_2}{\overset{\text{Al(CH}_3)_3}{\longrightarrow}} \text{I}$$
$$\underset{\text{VI}}{\overset{|}{\text{R}}}$$

wherein E, A, R, $L_1$, $L_2$, and $R_1$ are as defined above except $R_1$ is not $CO_2R_2$.

The reaction of Equation 4 is best carried out in methylene chloride at 25° to 40° C. for 24 to 96 hours under a nitrogen atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride or ether or by column chromatography.

Further details of this reaction and the preparation of the carbamates of Formula VI can be found in unexamined European Patent Application No. 83,975 (published July 20, 1983).

The preparation of compounds of Formula I of this invention is not limited to those methods described in Equation 1 and Equation 4. The compounds of Formula I also can be prepared by other methods known to those skilled in the art. For example, the compounds of Formula I can be prepared by methods analogous to those described in South African Patent Application No. 825042 and South African Patent Application No. 830441.

The synthesis of heterocyclic amine intermediates such as those depicted by Formula III has been reviewed in "The Chemistry of Heterocyclic Compounds", a series published by Interscience Publ., New York and London. Aminopyrimidines are described by D. J. Brown in the "Pyrimidines", Vol. VI of the above series.

The 5,6-dihydrofuro[2,3-d]pyrimidin-2-amines, the cyclopenta[d]pyrimidin-2-amines (A-2) and the 6,7-dihydro-5H-pyrano[2,3-d]pyrimidin-2-amines (A-3), are prepared as described in unexamined European Patent Application No. 15,683. Synthesis of the furo[2,3-d]pyrimidin-2-amines (A-4) are described in unexamined European Patent Application No. 46,677. The heterocyclic amines in which A is a triazole ring (A-5) are disclosed in U.S. Pat. No. 4,421,550 (issued Dec. 20, 1983). Pyrimidine and triazine amines in which Y is dialkoxymethyl or 1,3-dioxolan-2-yl are prepared as described in unexamined European Patent Application No. 84,224 (published July 27, 1983).

The biphenylsulfonamides and phenoxybenzenesulfonamides of Formula IV are also important intermediates for the preparation of the compounds of this invention. They can be prepared by the application of an appropriate method selected from the variety of known literature procedures for substituted benzenesulfonamide synthesis.

Many of the sulfonamides of Formula IV are available from metalated derivatives of substituted biphenyls or phenoxybenzenes as shown in Equation 5. Of necessity, the reactions are limited to those cases in which $R_1$, $L_1$ and $L_2$ are inert to lithium reagents under the conditions employed. For a general review of metallation with lithium reagents, see H. W. Gschwend and R. Rodriguez, Org. Reactions, 26, 1 (1979).

Equation 5

(a)

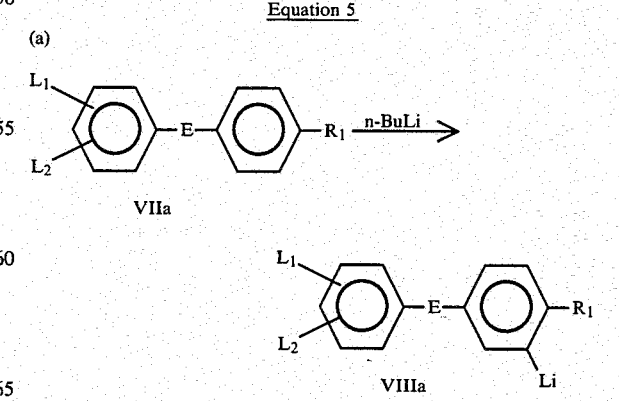

wherein $R_1$ is $SO_2NR_4R_5$, $SO_2N(OCH_3)CH_3$, $CONR_4R_5$, and $L_1$ is not $NO_2$, $R_4$ is not H.

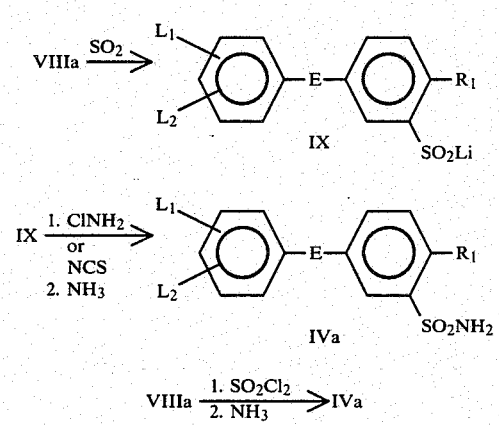

(b)

(c)

(d)

The reaction in Equation 5a is best carried out under nitrogen in an anhydrous, aprotic solvent such as tetrahydrofuran or diethyl ether with at least one equivalent of an alkyllithium reagent such as n-butyllithium at temperatures between −110° and 0° C. for 15 minutes to two hours. Sulfur dioxide is then added and the mixture allowed to slowly warm to ambient temperature over 1 to 4 hours. The crude sulfinate salt IX may be treated with an aqueous solution of chloramine to afford sulfonamide IVa. Alternatively, IX can first be oxidized with N-chlorosuccinimide (NCS) in a suitable solvent such as acetic acid and the resulting sulfonyl chloride is then treated with ammonia in a suitable solvent such as tetrahydrofuran to afford sulfonamide IVa. In addition, the lithiated species VIIIa may be treated directly with sulfuryl chloride below 0° C. as depicted in Equation 5c, and the intermediate sulfonyl chloride is then aminated as above to yield IVa.

For the preparation of sulfonamides IVa in which $R_1$ is an ester functionality, a suitably protected form of $R_1$ is desirable for reaction 5a. For example, a carboxamide or preferably a 4,4-dimethyloxazolin-2-yl moiety provides both protection from attack of the lithium reagent on $R_1$ and directs the position of metallation to an adjacent carbon on the benzene ring. The use of this technique and the preparation of species such as VIIIb is described by H. W. Gschwend and A. Hamdan [*J. Org. Chem.*, 40, 2008 (1975)].

Equation 6

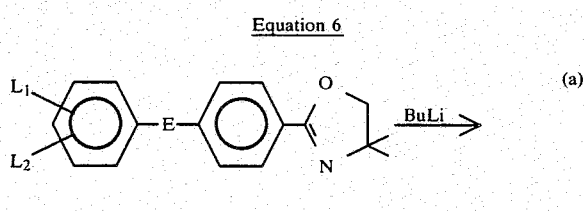

(a)

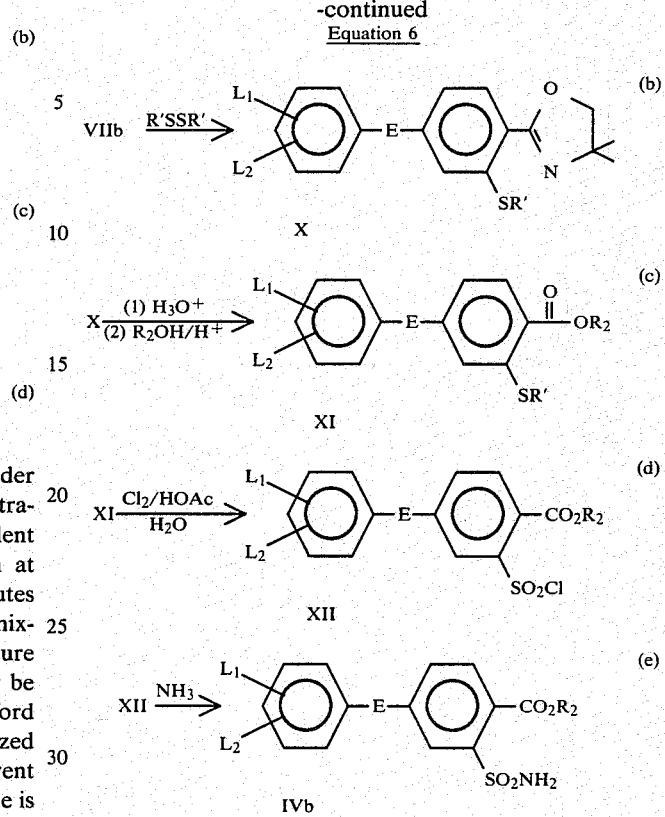

wherein
R' is lower alkyl and
$L_1$, $L_2$, $R_2$, and E are as defined above.

Further reactions of species such as VIIIb are best carried on to sulfonamides IVb via the alkylthio derivatives X, as depicted in reactions 6b through 6e. In reaction 6a, the metallated species VIIIb is formed under the same conditions described for reaction 5a and is then reacted with an alkyldisulfide to afford X as shown in 6b. The protecting oxazolidine ring is then cleaved by heating in aqueous mineral acid for 2–24 hours, and the product is subsequently esterified with the appropriate alcohol, $R_2OH$, under standard conditions using an acid catalyst such as sulfuric acid to give XI. Chlorination of XI in a suitable solvent such as acetic acid containing at least two equivalents of water yields the sulfonyl chloride XII as depicted in reaction 6d. The preferred temperature for the reaction of 6d is within the range of 0° to 20° C. Treatment of XII with ammonia as shown in reaction 6e affords the sulfonamide IVb.

When the substituent $R_1$ is located in the 2-position of the benzenesulfonamide IV as depicted in Equation 7, the methodologies outlined for Equations 5 and 6 above may also be applied to the conversion of XIII into IVc.

Equation 7

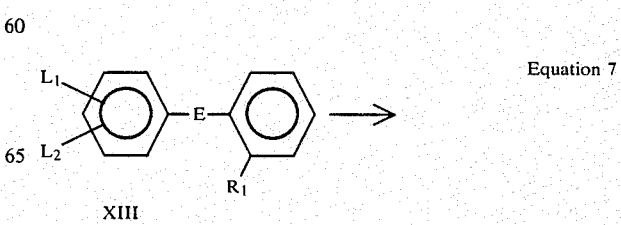

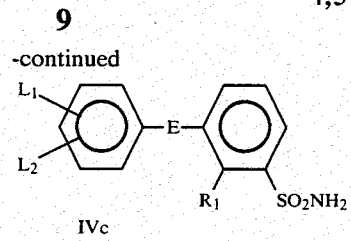

IVc wherein E, L$_1$, L$_2$, and R$_1$ are as defined in Equations 5 and 6.

Many sulfonamides of Formula IV may also be prepared by the sequence of reactions outlined in Equation 8.

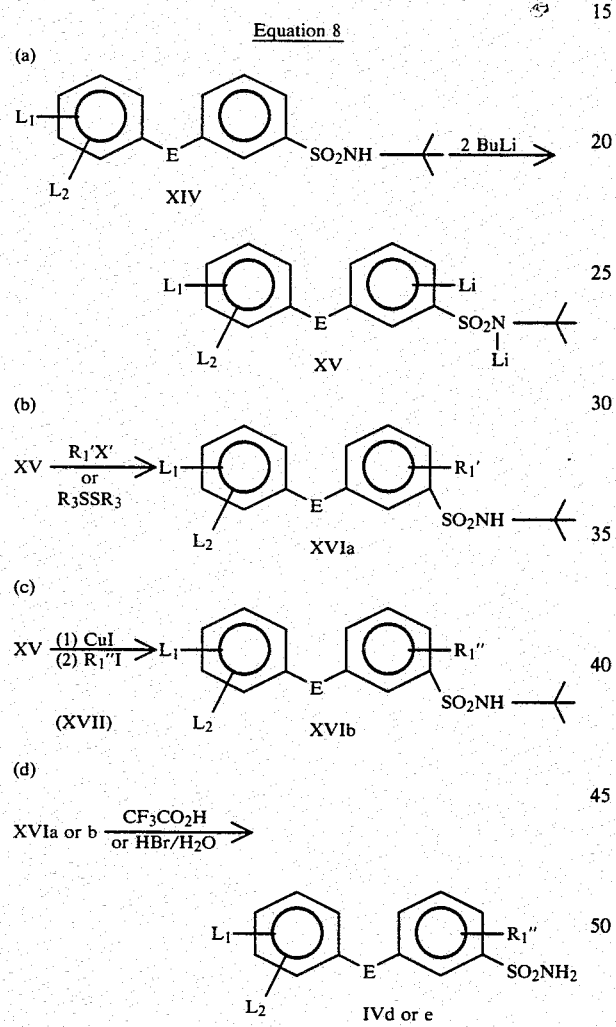

wherein E, L$_1$, L$_2$, R$_1$ and R$_3$ are as defined previously except L$_1$, is not NO$_2$; R$_1'$ is C$_1$-C$_2$ alkyl substituted with OCH$_3$, OC$_2$H$_5$, CH$_2$CH$_2$Cl or CF$_3$; X' is a suitable leaving group such as Cl, Br, I or OSO$_2$C$_6$H$_5$; and R$_1''$ is a heterocyclic ring selected from those defined above for R$_1$.

The reactive intermediates of Formula XV are prepared by analogy with the teaching of J. G. Lombardino in J. Org. Chem., 36 1843 (1971). A N-t-butyl sulfonamide of Formula XIV is dissolved in an ethereal solvent, such as tetrahydrofuran, and at least two equivalents of n-butyllithium in hexane are added at 0°-25° C. After 1-5 hours at 0°-25° C., the dianion XV is formed and is treated directly as in reactions 8b and 8c. In reaction 8b, an alkylating agent R$_1'$X' or an alkyl disulfide R$_3$SSR$_3$ is added to afford compounds of Formula XVIa. In reaction 8c, one equivalent of a copper(I) salt is added at −20° to 0° C., followed by 1-1.5 equivalents of the desired heteroaromatic iodide (XVII). The reaction mixture is then heated at 40°-70° for 1-3 days, concentrated, poured onto aqueous ammonia, and filtered to provide the compound of Formula XVIb. The reaction of Formula 8d is conducted by heating a compound of Formula XVIa or b with 2-10 equivalents of trifluoracetic acid or aqueous HBr with or without an inert solvent at 30°-70° C. for 1-3 days. The product IVd may be isolated as a trifluoroacetate or hydrobromide salt by evaporation of solvent and excess acid and trituration with ether. The free base may be obtained by neutralization of the salt with aqueous base, extraction into an organic solvent, and concentration of the organic extracts.

The preparation of analogous sulfonamides, IV, in which R$_1$ is a heterocyclic moiety is outlined in more detail in the following copending applications: U.S. Ser. Nos. 428,806, 436,631, 437,325 and 437,367.

Application of the reactions of Equation 8 may give rise to isomeric mixtures of sulfonamide products, namely IVd and IVe. These isomers can be separated at a convenient stage of the synthetic sequence by crystallization or chromatography on silica gel. A predominance of one isomer can be expected based upon the ortho-directing capabilities of the substituents present. For example, when E is oxygen the isomer IVd would be predominant, while the other isomer, IVe, may be the major product when E is a single bond.

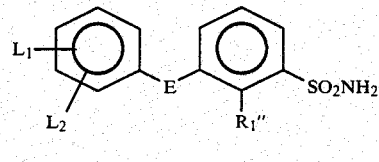

IVd (E = O)

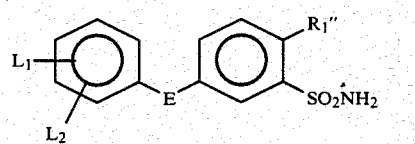

IVe (E = single bond)

Certain sulfonyl chloride precursors to sulfonamides of Formula IV may be prepared by more widely used methods than outlined above. For example, when R$_1$ is an electron rich substituent such as an alkoxy moiety, chlorosulfonation of the appropriately substituted biphenyl or phenoxybenzene in carbon tetrachloride may be used according to the teaching of H. T. Clarke et al. Org. Synth. Coll. Vol. I, 2nd Ed. 1941, p. 85. Other sulfonyl chloride precursors to sulfonamides IV are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, J. Org. Chem., 25, 1824 (1960).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

2-(1,1′-Biphenyl-4-yl)-4,5-dihydro-4,4-dimethyloxazole

A mixture of 30 g of 4-biphenylcarboxylic acid and 230 mL thionyl chloride was heated to reflux for 20 minutes then evaporated to dryness under reduced pressure to afford the solid acid chloride. This was dissolved in 75 mL $CH_2Cl_2$ and added to a solution of 27 mL 2-amino-2-methyl-1-propanol in 75 mL $CH_2Cl_2$ at 0°, then stirred 3 hours at ambient temperature. Solids were removed by filtration and the filtrate was slowly treated with 88.5 mL thionyl chloride then stirred 30 minutes at ambient temperature. The mixture was then evaporated to dryness and partitioned between ether and dilute sodium hydroxide solution. Crude product was obtained upon evaporation of the dried ether layer and was purified by chromatography on silica gel to afford 20 g of the title compound, mp 55°–58° (crystallized from hexanes).

EXAMPLE 2

2-(3-Methylthio-1,1′-biphenyl-4-yl)-4,5-dihydro-4,4-dimethyloxazole

A stirred solution of 13.3 g of the biphenyl oxazoline of Example 1 in 210 mL tetrahydrofuran (THF) was treated with 36 mL of 1.6M n-butyllithium in hexanes at $<-70°$ under nitrogen atmosphere. The mixture was kept at ca. $-40°$ for 50 min., then 5.2 mL methyl disulfide was added and the mixture slowly warmed to room temperature. After 2 days the solution was poured into ether and water, the organic phase was washed successively with saturated sodium bicarbonate solution, brine, then dried and evaporated. Trituration of the residue with n-chlorobutane plus hexanes gave 10.9 g of the title compound, mp 93°–95°.

EXAMPLE 3

Methyl 2-(methylthio)-4-phenylbenzoate

A mixture of 9.75 g of the oxazoline of Example 2 was hydrolyzed by refluxing in 200 mL of 6N HCl for 4 hours. Upon cooling, the free carboxylic acid crystallized out and was collected by filtration and dried to 7.8 g of white powder, mp 213°–5°. This was dissolved in 200 mL methanol with 2.0 mL sulfuric acid (conc.) and heated to reflux for 3 days. The methanol was removed by evaporation and the residue dissolved in ether and washed with sat. sodium bicarbonate solution. Evaporation of the dried ether extract and trituration with n-chlorobutane/hexanes gave 7.0 g of the title ester, mp 83°–85°. NMR ($CDCl_3$, 60 MHz): δ2.5 (s, 3H), 3.85 (s, 3H), 7.2–7.7 (m, 7H), 8.1 (d, J=8 Hz, 1H) ppm; IR (nujol) 1705 $cm^{-1}$.

EXAMPLE 4

Methyl 2-(chlorosulfonyl)-4-phenylbenzoate

A solution of 6.5 g of the sulfide of Example 3 was stirred in 100 mL acetic acid plus 2 mL water while chlorine gas was bubbled into the liquid with stirring. The temperature was kept at ca. 20° with the intermittent use of an ice bath. After 30 minutes an excess of chlorine was present, and subsequently the mixture was stirred at ambient temperature for 1 hour, then poured into 500 mL ice water. The sulfonyl chloride was extracted with methylene chloride, washed twice with 2N aqueous NaOH solution, once with water, dried ($MgSO_4$) and evaporated. Trituration of the residue with n-chlorobutane/hexanes afforded 5.8 g of the title compound, mp 77°–79°. NMR ($CDCl_3$, 200 MHz): δ4.0 (s, 3H), 7.45–7.65 (m, 5H), 7.8 (d, J=8 Hz, 1H), 7.95 (d of d, J=2, 8 Hz, 1H), 8.38 (d, J=2 Hz, 1H) ppm. IR (nujol) 1730 $cm^{-1}$.

EXAMPLE 5

Methyl 2-(Aminosulfonyl)-4-phenylbenzoate

The sulfonyl chloride of Example 4 (5.8 g) was stirred in 80 mL THF and treated with ammonia via a gas addition tube at ca. 15° for 15 min. The reaction mixture was then partitioned between ethyl acetate and dilute HCl. Evaporation of the dried organic phase gave a residue which was crystallized from n-chlorobutane to yield 5.3 g of the title sulfonamide, mp 146° (dec. to high melting solid). IR (nujol) 3320, 3220, 1715, 1330, 1170 $cm^{-1}$.

EXAMPLE 6

2-Carbomethoxy-4-phenylbenzenesulfonyl isocyanate

The sulfonamide of Example 5 (5.0 g) was stirred in 75 mL dry xylenes with 0.1 g DABCO ® and 1.9 mL n-butylisocyanate, then heated to reflux (138°) with a dry ice condenser in place. Phosgene gas was introduced into the vessel above the liquid level until the reaction temperature dropped below 130°. As phosgene was absorbed by the reactants, a gradual rise in reaction temperature was observed. Heating was continued until the reaction temperature remained constant, indicating complete consumption of the sulfonamide starting material (ca. 2 hrs). Evaporation of the xylenes after filtration under nitrogen to remove traces of solids gave crude sulfonyl isocyanate as a viscous oil. IR (neat) 2250 $cm^{-1}$.

EXAMPLE 7

Methyl 2-[[(4,6-dimethoxypyrimidin-2-yl)aminocarbonyl]aminosulfonyl]-4-phenylbenzoate A suspension of 0.28 g 2-amino-4,6-dimethoxypyrimidine in 7 mL dry acetonitrile was treated with 0.90 g of the isocyanate of Example 6 in 1.0 mL acetonitrile under nitrogen atmosphere. The mixture immediately became homogeneous, and subsequently a precipitate formed which was collected by filtration, rinsed with ether and dried to afford 0.5 g of the title compound, mp 204°–206°. NMR (CDCl$_3$, 200 MHz): δ3.86 (s, 3H), 4.00 (3, 6H), 5.78 (s, 1H), 7.20 (NH), 7.5 (m, 3H), 7.75 (m, 2H), 7.85 (m, 2H), 8.61 (d, J=2, 1H), 12.6 (br, NH) ppm; IR (nujol) 1730, 1710 cm$^{-1}$.

EXAMPLE 8

Methyl 2-[[(4-methoxy-6-methyl-1,3,5-triazin-2-yl)aminocarbonyl]aminosulfonyl]-4-phenylbenzoate A suspension of 0.32 g 2-amino-4-methoxy-6-methyl-1,3,5-triazine in 7 mL dry acetonitrile was treated with 0.90 g of the isocyanate of Example 6 in 1.0 mL acetonitrile under nitrogen atomosphere. The heterogeneous mixture was refluxed for 24 hours, then cooled and filtered to remove unreacted triazineamine. The filtrate was evaporated and the residue crystallized from a mixture of n-chlorobutane, methylene chloride and ether to afford 0.36 g of the title compound, mp 198°–200°. NMR (CDCl$_3$, 200 MHz): δ2.62 (s, 3H), 3.96 (s, 3H), 4.06 (s, 3H), 7.48 (m, 3H and NH), 7.70 (m, 2H), 7.84 (m, 2H), 8.6 (d, J=2 Hz, 1H), 12.55 (br, NH) ppm; IR (nujol) 1715, 1720 (sh) cm$^{-1}$.

EXAMPLE 9

2-Carbomethoxy-4-phenoxybenzenesulfonyl isocyanate

A solution of 1.8 g of methyl 2-(aminosulfonyl)-4-phenoxybenzoate (prepared by methods analogous to the sulfonamide of Example 5) in 15 mL chlorobenzene was treated with 0.55 mL of chlorosulfonyl isocyanate at room temperature, then heated to 100° for ca. 2 hours. The dark mixture was then cooled, decanted from some tarry residue and evaporated under reduced pressure. The title compound was indicated by the presence of a band at 2240 cm$^{-1}$ in the infrared spectrum (neat liquid). It was used without further purification.

EXAMPLE 10

Methyl 2-[[(4,6-dimethoxypyrimidin-2-yl)aminocarbonyl]aminosulfonyl]-4-phenoxybenzoate A suspension of 0.5 g 2-amino-4,6-dimethoxypyrimidine in 10 mL dry acetonitrile was treated with 1.9 g of 2-carbomethoxy-4-phenoxybenzenesulfonyl isocyanate, then stirred at ambient temperature overnight. The mixture was then evaporated to dryness and chromatographed on silica gel with 10% ethyl acetate in methylene chloride as an eluant. Product containing fractions were evaporated and crystallized from ether/hexanes to afford 0.2 g of the title compound, mp 163°–167°. NMR (CDCl$_3$, 90 MHz): δ3.85 (s, 3H), 4.00 (s, 6H), 5.80 (s, 1H), 7.0–7.55 (m, 7H), 7.75 (d, J=7 Hz, 1H), 8.1 (br, NH), 12.75 (br, NH) ppm; IR (nujol) 1730, 1710 cm$^{-1}$.

EXAMPLE 11

4-[(Dimethylamino)sulfonyl][1,1'-biphenyl]-3-sulfonyl chloride

A solution of 15.6 g N,N-dimethyl-[1,1'-biphenyl]-4-sulfonamide in 240 mL anhydrous THF was treated with 44 mL of 1.6M n-butyllithium in hexanes with the temperature kept below −60°. The mixture was stirred at −20° for 30 min. then recooled to below −60° while 5 mL of liquid sulfur dioxide was added dropwise. The cooling bath was removed and when the temperature had reached approx. 20°, the reaction mixture was evaporated to dryness under reduced pressure to a solid lithium sulfinate salt. This solid was dissolved in 400 mL of acetic acid then treated with 9.5 g of N-chlorosuccinimide in portions, keeping the temperature below 50°. After stirring at room temperature overnight, the solids were filtered off, rinsed with acetic acid and the filtrate treated with 1 g sodium bisulfite and evaporated to dryness. The residue was crystallized from methylene chloride, then triturated with cold 10% sodium hydroxide solution, filtered and rinsed with water. An additional quantity was obtained from the original acetic acid insoluble solids by washing with 10% sodium hydroxide solution and water. After drying, a total of 9.1 g of the title compound was obtained, mp 140°–143°: NMR (CDCl$_3$, 90 MHz): δ2.98 (s, 6H), 7.55 (m, 5H), 8.05 (d of d, J=2, 8 Hz, 1H), 8.32 (d, J=8 Hz, 1H), 8.65 (d, J=2 Hz, 1H) ppm.

EXAMPLE 12

N',N'-Dimethyl-4-phenyl-1,2-benzenedisulfonamide

A solution of 9.1 g of the sulfonyl chloride of Example 11 in 180 mL THF was treated with excess ammonia gas at room temperature for 20 min. The mixture was then filtered, rinsed with THF, the filtrate then evaporated to a solid residue. This was triturated with dilute aqueous HCl, filtered and rinsed with water and dried to 8.3 g of the title compound, mp 197°–200°. NMR (CDCl$_3$/DMSO-d$_6$, 90 MHz): δ2.98 (s, 6H), 7.0 (br, NH$_2$), 7.65 (m, 5H), 8.08 (m, 2H), 8.63 (d, J=2 Hz, 1H) ppm; IR (nujol) 3250, 3380, 1330, 1350, 1150, 1160, 1175 cm$^{-1}$.

EXAMPLE 13

2-[N,N-(Dimethylamino)sulfonyl]-5-phenylbenzenesulfonyl isocyanate

In 100 mL dry xylenes was placed 8.0 g of N',N'-dimethyl-4-phenyl-1,2-benzenedisulfonamide, 3.6 mL n-butyl isocyanate, and 0.2 g DABCO ® and heated to reflux (138°). Excess phosgene gas was introduced as in Example 6 and after 6 hours the mixture was cooled, filtered under nitrogen atmosphere and evaporated to a viscous oil, ca. 10 g. An infrared spectrum (neat) of this product exhibited an absorption at 2230 cm$^{-1}$, indicating the title compound.

EXAMPLE 14

N',N'-Dimethyl-N''-[(4-methoxy-6-methylpyrimidin-2-yl)aminocarbonyl]-4-phenyl-1,2-benzenedisulfonamide A solution of 0.41 g 2-amino-4-methoxy-6-methylpyrimidine in 4 mL dry acetonitrile was treated with 1.4 g of sulfonyl isocyanate of Example 13 in 1.5 mL acetonitrile. A precipitate formed immediately, which was collected and rinsed with n-chlorobutane to afford 1.28 g of the title compound, mp 198°–200° (dec.); NMR (CDCl₃, 90 MHz): δ2.48 (s, 3H), 2.97 (s, 6H), 3.97 (s, 3H), 6.29 (s, 1H), 7.25 (br, NH), 7.4–7.7 (m, 5H), 7.9 (d of d, J=2, 7 Hz, 1H), 8.11 (d, J=7 Hz, 1H), 8.85 (d, J=2 Hz, 1H), 13.15 (br, NH) ppm: IR (nujol) cm⁻¹.

By applying one or more of the methods described in Examples 1 through 14 and/or the techniques outlined above, the compounds of Tables I through VI may be prepared.

TABLE Ia

| R₁ | R | L₁ | L₂ | X | Y | m.p.(°C.) |
|---|---|---|---|---|---|---|
| 6-CO₂CH₃ | H | H | H | CH₃ | CH₃ | 204–206 |
| 6-CO₂CH₃ | H | H | H | OCH₃ | CH₃ | 181–183 |
| 6-CO₂CH₃ | H | H | H | OCH₃ | OCH₃ | 190–194 |
| 6-CO₂CH₃ | CH₃ | H | H | OCH₃ | CH₃ | |
| 6-CO₂CH₃ | H | H | H | OC₂H₅ | CH₃ | 175–177 |
| 6-CO₂CH₃ | H | H | H | Cl | OCH₃ | |
| 6-CO₂CH₃ | H | 4'-Cl | H | Br | OCH₃ | |
| 6-CO₂CH₃ | H | 4'-CH₃ | H | OCF₂H | OCH₃ | |
| 6-CO₂CH₃ | H | 2'-F | 4'-F | CF₃ | CF₃ | |
| 6-CO₂C₂H₅ | H | H | H | CH₂F | CH₃ | |
| 6-CO₂CH₃ | H | 2'-Cl | 4'-Cl | CH₃ | NH₂ | |
| 6-CO₂CH₃ | H | H | H | OCH₃ | NHCH₃ | |
| 6-CO₂CH₃ | H | H | H | CH₃ | N(CH₃)₂ | |
| 6-CO₂CH₃ | CH₃ | H | H | OCH₃ | CH₂OCH₃ | |
| 6-CO₂CH₃ | H | H | H | CH₃ | CH₂SCH₃ | |
| 6-CO₂CH₃ | H | H | H | OCH₃ | OCH₂CH=CH₂ | |
| 6-CO₂CH(CH₃)₂ | H | H | H | CH₃ | OCH₂C≡CH | |
| 2-CO₂CH₃ | H | 4'-Br | H | OCH₃ | OCH₂CF₃ | |
| 2-CO₂CH₃ | H | H | H | CH₃ | OCH₂CH₂OCH₃ | |
| 2-CO₂C₂H₅ | H | H | H | OCF₂H | OCF₂H | |
| 6-CO₂CH₂CH=CH₂ | H | H | H | OCH₃ | CH(OCH₃)₂ | |
| 6-CO₂CH₃ | H | 4'-OCH₃ | H | OCH₃ | (1,3-dioxolan-2-yl) | |
| 6-CO₂CH₃ | H | 4'-NO₂ | H | CH₃ | (1,3-dioxan-2-yl) | |
| 2-CO₂CH₃ | H | H | H | OCH₃ | (4-methyl-1,3-dioxolan-2-yl) | |
| 2-CO₂C₂H₅ | H | 3'-CH₃ | 4'-CH₃ | OCH₃ | CH(OC₂H₅)₂ | |
| 6-SCH₃ | H | 3'-Cl | 4'-Cl | CH₃ | SCH₃ | |
| 6-S(O)CH₃ | H | H | H | OCH₃ | C₂H₅ | |
| 2-SO₂CH₃ | H | H | H | OCH₃ | H | |
| 6-SC₂H₅ | H | H | H | CH₃ | H | |
| 6-SO₂CH₂CH₂CH₃ | H | 4'-CH₃ | 2'-Cl | CH₃ | CH₃ | |
| 6-SCH₂CH=CH₂ | H | 4'-CF₃ | H | CH₃ | OCH₃ | |
| 2-SO₂CH₃ | H | 4'-Cl | H | OCH₃ | OCH₃ | |
| 6-SO₂CH₃ | H | H | H | CH₃ | CH₃ | |
| 6-SO₂CH₃ | H | H | H | OCH₃ | CH₃ | |
| 6-SO₂CH₃ | H | H | H | OCH₃ | OCH₃ | |
| 6-SO₂N(CH₃)₂ | H | H | H | CH₃ | CH₃ | 221–224 |
| 6-SO₂N(CH₃)₂ | H | H | H | OCH₃ | CH₃ | 198–200 |
| 6-SO₂N(CH₃)₂ | H | H | H | OCH₃ | OCH₃ | 199–202 |
| 6-SO₂N(CH₃)₂ | H | H | H | OC₂H₅ | CH₃ | |
| 6-SO₂N(CH₃)₂ | H | H | H | Cl | OCH₃ | 144–146 |
| 6-SO₂N(CH₃)₂ | H | 4'-Cl | H | Br | OCH₃ | |
| 6-SO₂N(CH₃)₂ | H | H | H | OCF₂H | OCH₃ | |
| 2-SO₂N(CH₃)₂ | H | H | H | CF₃ | CF₃ | |
| 2-SO₂N(CH₃)₂ | H | H | H | CH₂F | CH₃ | |
| 2-SO₂N(CH₃)₂ | CH₃ | H | H | CH₃ | NH₂ | |
| 2-SO₂N(CH₃)₂ | H | 2'-Cl | 4'-Cl | OCH₃ | NHCH₃ | |
| 6-SO₂N(CH₃)C₂H₅ | H | H | H | CH₃ | N(CH₃)₂ | |

TABLE Ia-continued

| R₁ | R | L₁ | L₂ | X | Y | m.p.(°C.) |
|---|---|---|---|---|---|---|
| 6-SO$_2$NHCH$_3$ | H | H | H | OCH$_3$ | CH$_2$OCH$_3$ | |
| 6-SO$_2$N(C$_2$H$_5$)$_2$ | H | H | H | CH$_3$ | OCH$_2$C≡CH | |
| 6-SO$_2$N(OCH$_3$)CH$_3$ | H | H | H | OCH$_3$ | OCH$_2$CF$_3$ | |
| 6-OSO$_2$CH$_3$ | H | 4'-F | H | CH$_3$ | OCH$_2$CH$_2$OCH$_3$ | |
| 6-OSO$_2$C$_2$H$_5$ | H | H | H | OCF$_2$H | OCF$_2$H | |
| 6-OSO$_2$CF$_3$ | H | H | H | OCH$_3$ | CH(OCH$_3$)$_2$ | |
| 2-OSO$_2$C$_2$H$_5$ | H | 4'-CH$_3$ | H | OCH$_3$ | (1,3-dioxolan-2-yl) | |
| 6-CF$_3$ | H | H | H | CH$_3$ | (1,3-dioxan-2-yl) | |
| 6-OCHF$_2$ | H | H | H | OCH$_3$ | (4-methyl-1,3-dioxolan-2-yl) | |
| 6-OCF$_3$ | H | H | H | OCH$_3$ | CH(OC$_2$H$_5$)$_2$ | |
| 2-OCH$_2$CH=CH$_2$ | H | H | H | CH$_3$ | SCH$_3$ | |
| 6-OCH$_2$C≡CH | H | H | H | OCH$_3$ | C$_2$H$_5$ | |
| 6-OCH$_2$C≡C—CH$_3$ | H | H | H | OCH$_3$ | H | |
| 6-CH$_2$OCH$_3$ | CH$_3$ | H | H | CH$_3$ | H | |
| 6-CH$_2$OC$_2$H$_5$ | H | H | H | CH$_3$ | CH$_3$ | |
| 6-CH$_2$CH$_2$OCH$_3$ | H | H | H | CH$_3$ | OCH$_3$ | |
| 6-OSO$_2$CH$_3$ | H | H | H | OCH$_3$ | OCH$_3$ | |
| 2-SO$_2$N(CH$_3$)$_2$ | H | H | H | CH$_3$ | CH$_3$ | |
| 2-SO$_2$N(CH$_3$)$_2$ | H | 3'-F | H | OCH$_3$ | CH$_3$ | |
| 2-SO$_2$N(CH$_3$)$_2$ | H | 3'-Cl | 4'-Cl | OCH$_3$ | OCH$_3$ | |
| 6-(5-methyl-1,3,4-oxadiazol-2-yl) | H | H | H | CH$_3$ | CH$_3$ | |
| 6-(1,3,4-oxadiazol-2-yl) | H | 4'-Cl | H | OCH$_3$ | OCH$_3$ | |
| 6-(1,2,3-thiadiazol-4-yl) | H | H | H | Cl | OCH$_3$ | |
| 6-(furan-2-yl) | H | H | H | CH$_3$ | OCH$_3$ | |
| 6-(tetrahydrofuran-2-yl) | H | H | H | CH$_3$ | CH$_3$ | |

TABLE Ia-continued

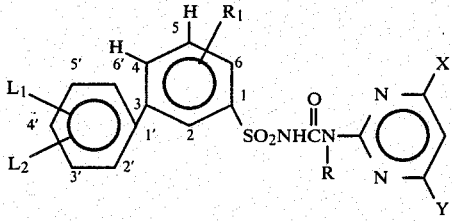

| $R_1$ | R | $L_1$ | $L_2$ | X | Y | m.p.(°C.) |
|---|---|---|---|---|---|---|
| 6- (oxazole) | H | H | H | $OCH_3$ | $OCH_3$ | |
| 6- (pyridyl) | H | H | H | $OCH_3$ | $OCH_3$ | |
| 6- (thienyl) | H | H | H | $OCH_3$ | $OCHF_2$ | |
| $6\text{-}CO_2CH_3$ | H | H | H | $CH_2Cl$ | $OCH_3$ | |
| $6\text{-}CO_2CH_3$ | H | H | H | $CH_2Br$ | $CH_3$ | |
| $6\text{-}CO_2CH_3$ | H | H | H | $CH_3$ | $-C(OCH_3)_2CH_3$ | |
| $6\text{-}CO_2CH_3$ | H | H | H | $CH_3$ | $N(OCH_3)CH_3$ | |
| $6\text{-}CO_2CH_3$ | H | H | H | $OCH_3$ | cyclopropyl | |
| $6\text{-}SO_2CH_3$ | H | H | H | $OCH_2CH_3$ | $N(OCH_3)CH_3$ | |
| $6\text{-}SO_2N(CH_3)_2$ | H | H | H | $CF_3$ | $N(OCH_3)CH_3$ | |
| $6\text{-}OSO_2CH_3$ | H | H | H | $OCF_2H$ | cyclopropyl | |
| $6\text{-}OCH_2CH=CH_2$ | H | H | H | $CFH_2$ | cyclopropyl | |

TABLE Ib

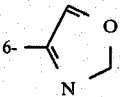

| $R_1$ | R | $L_1$ | $L_2$ | X | Y | m.p. (°C) |
|---|---|---|---|---|---|---|
| $6\text{-}CO_2CH_3$ | H | H | H | $CH_3$ | $CH_3$ | |
| $6\text{-}CO_2CH_3$ | H | H | H | $OCH_3$ | $CH_3$ | |
| $6\text{-}CO_2CH_3$ | H | H | H | $OCH_3$ | $OCH_3$ | 163–167 |
| $6\text{-}CO_2CH_3$ | $CH_3$ | H | H | $OCH_3$ | $CH_3$ | |

TABLE Ib-continued

| R₁ | R | L₁ | L₂ | X | Y | m.p. (°C) |
|---|---|---|---|---|---|---|
| 6-CO$_2$CH$_3$ | H | H | H | OC$_2$H$_5$ | CH$_3$ | |
| 6-CO$_2$CH$_3$ | H | H | H | Cl | OCH$_3$ | |
| 6-CO$_2$CH$_3$ | H | 4'-Cl | H | Br | OCH$_3$ | |
| 6-CO$_2$CH$_3$ | H | 4'-CH$_3$ | H | OCF$_2$H | OCH$_3$ | |
| 6-CO$_2$CH$_3$ | H | 2'-F | 4'-F | CF$_3$ | CF$_3$ | |
| 6-CO$_2$C$_2$H$_5$ | H | H | H | CH$_2$F | CH$_3$ | |
| 6-CO$_2$CH$_3$ | H | 2'-Cl | 4'-Cl | CH$_3$ | NH$_2$ | |
| 6-CO$_2$CH$_3$ | H | H | H | OCH$_3$ | NHCH$_3$ | |
| 6-CO$_2$CH$_3$ | H | H | H | CH$_3$ | N(CH$_3$)$_2$ | |
| 6-CO$_2$CH$_3$ | CH$_3$ | H | H | OCH$_3$ | CH$_2$OCH$_3$ | |
| 6-CO$_2$CH$_3$ | H | H | H | CH$_3$ | CH$_2$SCH$_3$ | |
| 6-CO$_2$CH$_3$ | H | H | H | OCH$_3$ | OCH$_2$CH=CH$_2$ | |
| 6-CO$_2$CH(CH$_3$)$_2$ | H | H | H | CH$_3$ | OCH$_2$C≡CH | |
| 2-CO$_2$CH$_3$ | H | 4'-Br | H | OCH$_3$ | OCH$_2$CF$_3$ | |
| 2-CO$_2$CH$_3$ | H | H | H | CH$_3$ | OCH$_2$CH$_2$OCH$_3$ | |
| 2-CO$_2$C$_2$H$_5$ | H | H | H | OCF$_2$H | OCF$_2$H | |
| 6-CO$_2$CH$_2$CH=CH$_2$ | H | H | H | OCH$_3$ | CH(OCH$_3$)$_2$ | |
| 6-CO$_2$CH$_3$ | H | 4'-OCH$_3$ | H | OCH$_3$ | ![dioxolane -CH with two O-CH$_2$-CH$_2$] | |
| 6-CO$_2$CH$_3$ | H | 4'-NO$_2$ | H | CH$_3$ | ![dioxane -CH with O-CH$_2$-CH$_2$-CH$_2$-O] | |
| 2-CO$_2$CH$_3$ | H | H | H | OCH$_3$ | ![-CH(O-CH$_2$-CH(CH$_3$)-O)] | |
| 2-CO$_2$C$_2$H$_5$ | H | 3'-CH$_3$ | 4'-CH$_3$ | OCH$_3$ | CH(OC$_2$H$_5$)$_2$ | |
| 6-SCH$_3$ | H | 3'-Cl | 4'-Cl | CH$_3$ | SCH$_3$ | |
| 6-S(O)CH$_3$ | H | H | H | OCH$_3$ | C$_2$H$_5$ | |
| 2-SO$_2$CH$_3$ | H | H | H | OCH$_3$ | H | |
| 6-SC$_2$H$_5$ | H | H | H | CH$_3$ | H | |
| 6-SO$_2$CH$_2$CH$_2$CH$_3$ | H | 4'-CH$_3$ | 2'-Cl | CH$_3$ | CH$_3$ | |
| 6-SCH$_2$CH=CH$_3$ | H | 4'-CF$_3$ | H | CH$_3$ | OCH$_3$ | |
| 2-SO$_2$CH$_3$ | H | 4'-Cl | H | OCH$_3$ | OCH$_3$ | |
| 6-SO$_2$CH$_3$ | H | H | H | CH$_3$ | CH$_3$ | |
| 6-SO$_2$CH$_3$ | H | H | H | OCH$_3$ | CH$_3$ | |
| 6-SO$_2$CH$_3$ | H | H | H | OCH$_3$ | OCH$_3$ | |
| 6-SO$_2$N(CH$_3$)$_2$ | H | H | H | CH$_3$ | CH$_3$ | |
| 6-SO$_2$N(CH$_3$)$_2$ | H | H | H | OCH$_3$ | CH$_3$ | |
| 6-SO$_2$N(CH$_3$)$_2$ | H | H | H | OCH$_3$ | OCH$_3$ | |
| 6-SO$_2$N(CH$_3$)$_2$ | H | H | H | OCH$_3$ | CH$_3$ | |
| 6-SO$_2$N(CH$_3$)$_2$ | H | H | H | OC$_2$H$_5$ | CH$_3$ | |
| 6-SO$_2$N(CH$_3$)$_2$ | H | H | H | Cl | OCH$_3$ | |
| 6-SO$_2$N(CH$_3$)$_2$ | H | 4'-Cl | H | Br | OCH$_3$ | |
| 6-SO$_2$N(CH$_3$)$_2$ | H | H | H | OCF$_2$H | OCH$_3$ | |
| 2-SO$_2$N(CH$_3$)$_2$ | H | H | H | CF$_3$ | CF$_3$ | |
| 2-SO$_2$N(CH$_3$)$_2$ | H | H | H | CH$_2$F | CH$_3$ | |
| 2-SO$_2$N(CH$_3$)$_2$ | CH$_3$ | H | H | CH$_3$ | NH$_2$ | |
| 2-SO$_2$N(CH$_3$)$_2$ | H | 2'-Cl | 4'-Cl | OCH$_3$ | NHCH$_3$ | |
| 6-SO$_2$N(CH$_3$)C$_2$H$_5$ | H | H | H | CH$_3$ | N(CH$_3$)$_2$ | |
| 6-SO$_2$NHCH$_3$ | H | H | H | OCH$_3$ | CH$_2$OCH$_3$ | |
| 6-SO$_2$N(C$_2$H$_5$)$_2$ | H | H | H | CH$_3$ | OCH$_2$C≡CH | |
| 6-SO$_2$N(OCH$_3$)CH$_3$ | H | H | H | OCH$_3$ | OCH$_2$CF$_3$ | |
| 6-OSO$_2$CH$_3$ | H | 4'-F | H | CH$_3$ | OCH$_2$CH$_2$OCH$_3$ | |
| 6-OSO$_2$C$_2$H$_5$ | H | H | H | OCF$_2$H | OCF$_2$H | |
| 6-OSO$_2$CF$_3$ | H | H | H | OCH$_3$ | CH(OCH$_3$)$_2$ | |

TABLE Ib-continued

Structure: Diphenyl ether with sulfonylurea linked to pyrimidine. Phenyl ring 1 bears $L_1$ (4' or other) and $L_2$ (3' or other); phenyl ring 2 bears $R_1$; linked via $-SO_2NHC(O)N(R)-$ to a pyrimidine with substituents X and Y.

| $R_1$ | R | $L_1$ | $L_2$ | X | Y | m.p. (°C) |
|---|---|---|---|---|---|---|
| 2-OSO$_2$C$_2$H$_5$ | H | 4'-CH$_3$ | H | OCH$_3$ | 1,3-dioxolan-2-yl | |
| 6-CF$_3$ | H | H | H | CH$_3$ | 1,3-dioxan-2-yl | |
| 6-OCHF$_2$ | H | H | H | OCH$_3$ | 4-methyl-1,3-dioxolan-2-yl | |
| 6-OCF$_3$ | H | H | H | OCH$_3$ | CH(OC$_2$H$_5$)$_2$ | |
| 2-OCH$_2$CH=CH$_2$ | H | H | H | CH$_3$ | SCH$_3$ | |
| 6-OCH$_2$C≡CH | H | H | H | OCH$_3$ | C$_2$H$_5$ | |
| 6-OCH$_2$C≡C—CH$_3$ | H | H | H | OCH$_3$ | H | |
| 6-CH$_2$OCH$_3$ | CH$_3$ | H | H | CH$_3$ | H | |
| 6-CH$_2$OC$_2$H$_5$ | H | H | H | CH$_3$ | CH$_3$ | |
| 6-CH$_2$CH$_2$OCH$_3$ | H | H | H | CH$_3$ | OCH$_3$ | |
| 6-OSO$_2$CH$_3$ | H | H | H | OCH$_3$ | OCH$_3$ | |
| 2-SO$_2$N(CH$_3$)$_2$ | H | H | H | CH$_3$ | CH$_3$ | |
| 2-SO$_2$N(CH$_3$)$_2$ | H | 3'-F | H | OCH$_3$ | CH$_3$ | |
| 2-SO$_2$N(CH$_3$)$_2$ | H | 3'-Cl | 4'-Cl | OCH$_3$ | OCH$_3$ | |
| 6-(5-methyl-1,3,4-oxadiazol-2-yl) | H | H | H | CH$_3$ | CH$_3$ | |
| 6-(1,3,4-oxadiazol-2-yl) | H | 4'-Cl | H | OCH$_3$ | OCH$_3$ | |
| 6-(1,2,3-thiadiazol-4-yl) | H | H | H | Cl | OCH$_3$ | |
| 6-(furan-2-yl) | H | H | H | CH$_3$ | OCH$_3$ | |
| 6-(tetrahydrofuran-2-yl) | H | H | H | CH$_3$ | CH$_3$ | |
| 6-(oxazol-4-yl) | H | H | H | OCH$_3$ | OCH$_3$ | |

TABLE Ib-continued

| R₁ | R | L₁ | L₂ | X | Y | m.p. (°C) |
|---|---|---|---|---|---|---|
| 6-(2-pyridyl) | H | H | H | OCH₃ | OCH₃ | |
| 6-(2-thienyl) | H | H | H | OCH₃ | OCHF₂ | |
| 6-CO₂CH₃ | H | 4'-Cl | H | CH₃ | CH₃ | 185-187 |
| 6-CO₂CH₃ | H | 4'-Cl | H | CH₃ | OCH₃ | 125-135(d) |
| 6-CO₂CH₃ | H | 4'-Cl | H | OCH₃ | OCH₃ | 195-198 |
| 6-CO₂CH₃ | H | 4'-Cl | H | Cl | OCH₃ | 165-170 |
| 6-CO₂CH₃ | H | H | H | CH₂Cl | OCH₃ | |
| 6-CO₂CH₃ | H | H | H | CH₂Br | CH₃ | |
| 6-CO₂CO₂CH₃ | H | H | H | OCH₃ | —C(OCH₃)₂CH₃ | |
| 6-SO₂CH₃ | H | H | H | OCH₃ | N(OCH₃)CH₃ | |
| 6-CO₂CH₃ | H | H | H | CH₃ | N(OCH₃)CH₃ | |
| 6-SO₂N(CH₃)₂ | H | H | H | OCF₂H | N(OCH₃)CH₃ | |
| 6-CO₂CH₃ | H | H | H | CF₃ | N(OCH₃)CH₃ | |
| 6-OSO₂CH₃ | H | H | H | CH₃ | cyclopropyl-CH— | |
| 6-CO₂CH₃ | H | H | H | OCH₃ | cyclopropyl-CH— | |
| 6-SO₂N(CH₃)₂ | H | H | H | OCF₂H | cyclopropyl-CH— | |

TABLE IIa

| R₁ | R | L₁ | L₂ | X | Y | m.p. (°C.) |
|---|---|---|---|---|---|---|
| 6-CO₂CH₃ | H | H | H | CH₃ | OCH₃ | 198-200° |
| 6-CO₂CH₃ | H | H | H | OCH₃ | OCH₃ | 190-192° |
| 6-CO₂CH₃ | CH₃ | H | H | OCH₃ | OCH₃ | |
| 6-SO₂N(CH₃)₂ | H | H | H | CH₃ | OCH₃ | 192-195° |
| 6-SO₂N(CH₃)₂ | H | H | H | OCH₃ | OCH₃ | 175-179° |
| 6-SO₂N(CH₃)₂ | H | H | H | OCH₃ | N(CH₃)₂ | |
| 2-CO₂CH₃ | H | H | H | CH₃ | OCH₃ | |
| 6-OSO₂CH₃ | H | 4'-Cl | H | CH₃ | OCH₃ | |

TABLE IIa-continued

Structure: biphenyl with SO$_2$NHC(O)N(R)-triazine/pyrimidine bearing X and Y; L$_1$ at 5', L$_2$ at 3'; R$_1$ on right ring.

| R$_1$ | R | L$_1$ | L$_2$ | X | Y | m.p. (°C.) |
|---|---|---|---|---|---|---|
| 6-OCHF$_2$ | H | H | H | OCH$_3$ | OCH$_3$ | |
| 2-SO$_2$N(CH$_3$)$_2$ | H | H | H | OCH$_3$ | OCH$_2$CH=CH$_2$ | |
| 6-(1,2,3-thiadiazol-4-yl) | H | H | H | OCH$_3$ | OCF$_2$H | |
| 2-CF$_3$ | H | H | H | OCH$_3$ | CH$_3$ | |
| 2-SO$_2$CH$_3$ | H | H | H | CH$_3$ | OCH$_3$ | |
| 6-SO$_2$CH$_3$ | H | H | H | OCH$_3$ | OCH$_3$ | |
| 6-CH$_2$OCH$_3$ | H | H | H | OCH$_3$ | CH$_3$ | |
| 6-SO$_2$CH$_3$ | CH$_3$ | H | H | OCH$_3$ | CH$_3$ | |
| 6-(pyrazol-1-yl) | H | H | H | CH$_3$ | NHCH$_3$ | |
| 6-CH$_2$CH$_2$OCH$_3$ | H | H | H | CH$_3$ | CH(OCH$_3$)$_2$ | |
| 6-CH$_2$CH$_2$Cl | H | H | H | OCH$_3$ | NH$_2$ | |
| 2-CO$_2$CH$_3$ | H | H | H | OCH$_3$ | OCH$_3$ | |
| 2-CO$_2$CH$_3$ | H | H | H | CH$_3$ | CH$_3$ | |
| 2-SO$_2$N(CH$_3$)$_2$ | H | H | H | OCH$_3$ | CH$_3$ | |
| 2-SO$_2$N(CH$_3$)$_2$ | H | H | H | OCH$_3$ | OCH$_3$ | |
| 6-OCH$_2$CH=CH$_2$ | H | 4'-CH$_3$ | 2'-Cl | OCH$_3$ | SCH$_3$ | |
| 6-S(O)C$_2$H$_5$ | H | H | H | CH$_3$ | OCH$_2$CF$_3$ | |
| 6-CO$_2$CH$_3$ | H | H | H | CH$_2$Br | OCH$_3$ | |
| 6-CO$_2$CH$_3$ | H | H | H | OCH$_3$ | —C(OCH$_3$)$_2$CH$_3$ | |
| 6-CO$_2$CH$_3$ | H | H | H | OCH$_3$ | N(OCH$_3$)CH$_3$ | |
| 6-CO$_2$CH$_3$ | H | H | H | CH$_3$ | N(OCH$_3$)CH$_3$ | |
| 6-SO$_2$N(CH$_3$)$_2$ | H | H | H | OCF$_2$H | N(OCH$_3$)CH$_3$ | |
| 2-CO$_2$CH$_3$ | H | H | H | CH$_3$ | cyclopropyl | |
| 2-SO$_2$CH$_3$ | H | H | H | OCH$_3$ | cyclopropyl | |

TABLE IIb

Structure: diphenyl ether with SO$_2$NHC(O)N(R)-pyrimidine; L$_1$ at 5', L$_2$ at 3'; R$_1$ on right ring.

| R$_1$ | R | L$_1$ | L$_2$ | X | Y | m.p. (°C.) |
|---|---|---|---|---|---|---|
| 6-CO$_2$CH$_3$ | H | H | H | CH$_3$ | OCH$_3$ | |

TABLE IIb-continued

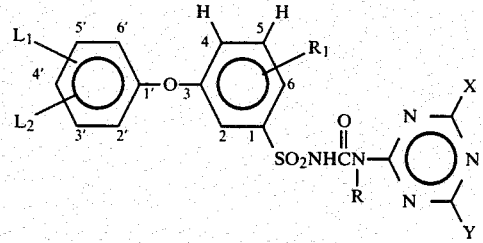

| R₁ | R | L₁ | L₂ | X | Y | m.p. (°C.) |
|---|---|---|---|---|---|---|
| 6-CO$_2$CH$_3$ | H | H | H | OCH$_3$ | OCH$_3$ | |
| 6-CO$_2$CH$_3$ | H | 4'-Cl | H | OCH$_3$ | OCH$_3$ | 175–178 |
| 6-CO$_2$CH$_3$ | CH$_3$ | H | H | OCH$_3$ | OCH$_3$ | |
| 6-SO$_2$N(CH$_3$)$_2$ | H | H | H | CH$_3$ | OCH$_3$ | |
| 6-SO$_2$N(CH$_3$)$_2$ | H | H | H | OCH$_3$ | OCH$_3$ | |
| 6-SO$_2$N(CH$_3$)$_2$ | H | H | H | OCH$_3$ | N(CH$_3$)$_2$ | |
| 2-CO$_2$CH$_3$ | H | H | H | CH$_3$ | OCH$_3$ | |
| 6-OSO$_2$CH$_3$ | H | 4'-Cl | H | CH$_3$ | OCH$_3$ | |
| 6-OCHF$_2$ | H | H | H | OCH$_3$ | OCH$_3$ | |
| 2-SO$_2$N(CH$_3$)$_2$ | H | H | H | OCH$_3$ | OCH$_2$CH=CH$_2$ | |
| 6-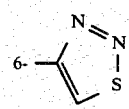 | H | H | H | OCH$_3$ | OCF$_2$H | |
| 2-CF$_3$ | H | H | H | OCH$_3$ | CH$_3$ | |
| 2-SO$_2$CH$_3$ | H | H | H | CH$_3$ | OCH$_3$ | |
| 6-SO$_2$CH$_3$ | H | H | H | OCH$_3$ | OCH$_3$ | |
| 6-CH$_2$OCH$_3$ | H | H | H | OCH$_3$ | CH$_3$ | |
| 6-SO$_2$CH$_3$ | CH$_3$ | H | H | OCH$_3$ | CH$_3$ | |
| 6-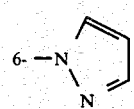 | H | H | H | CH$_3$ | NHCH$_3$ | |
| 6-CH$_2$CH$_2$OCH$_3$ | H | H | H | CH$_3$ | CH(OCH$_3$)$_2$ | |
| 6-CH$_2$CH$_2$Cl | H | H | H | OCH$_3$ | NH$_2$ | |
| 2-CO$_2$CH$_3$ | H | H | H | OCH$_3$ | OCH$_3$ | |
| 2-CO$_2$CH$_3$ | H | H | H | CH$_3$ | CH$_3$ | |
| 2-SO$_2$N(CH$_3$)$_2$ | H | H | H | OCH$_3$ | CH$_3$ | |
| 2-SO$_2$N(CH$_3$)$_2$ | H | H | H | OCH$_3$ | OCH$_3$ | |
| 6-OCH$_2$CH=CH$_2$ | H | 4'-CH$_3$ | 2'-Cl | OCH$_3$ | SCH$_3$ | |
| 6-S(O)C$_2$H$_5$ | H | H | H | CH$_3$ | OCH$_2$CF$_3$ | |
| 6-CO$_2$CH$_3$ | H | H | H | CH$_2$Br | CH$_3$ | |
| 6-CO$_2$CH$_3$ | H | H | H | OCH$_3$ | —C(OCH$_3$)$_2$CH$_3$ | |
| 6-CO$_2$CH$_3$ | H | H | H | CH$_3$ | N(OCH$_3$)CH$_3$ | |
| 6-CO$_2$CH$_3$ | H | H | H | OCH$_3$ | N(OCH$_3$)CH$_3$ | |
| 2-SO$_2$N(CH$_3$)$_2$ | H | H | H | OCF$_2$H | N(OCH$_3$)CH$_3$ | |
| 6-CO$_2$CH$_3$ | H | H | H | CH$_3$ | —CH(CH$_2$)(CH$_2$) | |
| 6-CO$_2$CH$_3$ | H | H | H | OCH$_3$ | —CH(CH$_2$)(CH$_2$) | |
| 2-SO$_2$CH$_3$ | H | H | H | CH$_2$F | —CH(CH$_2$)(CH$_2$) | |

TABLE III

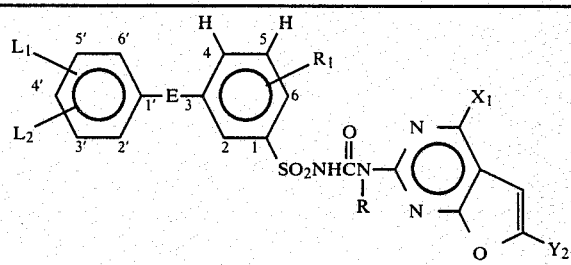

| R₁ | E | R | L₁ | L₂ | X₁ | Y₁ | m.p. (°C.) |
|---|---|---|---|---|---|---|---|
| 6-CO₂CH₃ | — | H | H | H | CH₃ | O | |
| 6-CO₂CH₃ | — | H | H | H | OCH₃ | O | |
| 6-CO₂CH₃ | — | H | H | H | CH₃ | CH₂ | |
| 6-CO₂CH₃ | O | H | 4'-CH₃ | 2'-Cl | OCH₃ | O | |
| 6-SO₂N(CH₃)₂ | O | H | H | H | OCH₃ | CH₂ | |
| 6-SO₂N(CH₃)₂ | — | H | H | H | OCH₃ | O | |
| 6-SO₂CH₃ | — | H | H | H | CH₃ | O | |
| 6-S(O)C₂H₅ | O | H | 4'-Cl | H | OCF₂H | O | |
| 6-CO₂C₂H₅ | — | H | H | H | OC₂H₅ | O | |
| 2-SCH₃ | — | CH₃ | H | H | CH₃ | CH₂ | |
| 2-SO₂N(C₂H₅)₂ | — | H | H | H | CH₃ | O | |

TABLE IV

| R₁ | E | R | L₁ | L₂ | X₁ | m.p. (°C.) |
|---|---|---|---|---|---|---|
| 6-CO₂CH₃ | — | H | H | H | CH₃ | |
| 6-CO₂CH₃ | — | H | H | H | OCH₃ | |
| 6-CO₂CH₃ | O | H | H | H | CH₃ | |
| 6-CO₂C₂H₅ | — | H | H | H | OCH₃ | |
| 2-CO₂CH₃ | — | H | H | H | CH₃ | |
| 6-SO₂N(CH₃)₂ | O | H | 4'-Cl | 2'-Cl | OCH₃ | |

TABLE IV-continued

| R₁ | E | R | L₁ | L₂ | X₁ | m.p. (°C.) |
|---|---|---|---|---|---|---|
| 6-SO₂N(CH₃)₂ | — | CH₃ | H | H | OC₂H₅ | |
| 6-(2-pyridyl) | O | H | H | H | OCHF₂ | |
| 6-OCHF₂ | — | H | 3'-CF₃ | H | CH₃ | |
| 6-OCH₂CH=CH₂ | — | H | H | H | CH₃ | |

TABLE V

| R₁ | E | R | L₁ | L₂ | X₁ | Y₂ | m.p. (°C.) |
|---|---|---|---|---|---|---|---|
| 6-CO₂CH₃ | — | H | H | H | CH₃ | CH₃ | |
| 6-CO₂CH₃ | — | H | H | H | OCH₃ | CH₃ | |
| 6-CO₂CH₃ | O | H | 4'-Cl | H | OC₂H₅ | H | |
| 6-SO₂CH₃ | — | H | H | H | OCH₃ | CH₃ | |
| 6-SO₂N(CH₃)₂ | O | H | H | H | OCH₃ | CH₃ | |
| 6-SO₂N(CH₃)₂ | — | CH₃ | H | H | CH₃ | H | |
| 6-SO₂N(OCH₃)CH₃ | O | H | H | H | CH₃ | CH₃ | |
| 2-OCHF₂ | — | H | 4'-CH₃ | 2'-Cl | CH₃ | CH₃ | |
| 2-CO₂CH₃ | O | H | H | H | OCF₂H | CH₃ | |
| 2-SO₂N(CH₃)₂ | — | H | H | H | CH₃ | CH₃ | |
| 6-CO₂CH₃ | O | H | 4'-F | H | CH₃ | H | |
| 6-SO₂N(CH₃)₂ | — | H | 4'-OCH₃ | H | CH₃ | H | |

TABLE VI

| R₁ | E | R | L₁ | L₂ | X₂ | Y₃ | m.p. (°C.) |
|---|---|---|---|---|---|---|---|
| 6-CO₂CH₃ | — | H | H | H | CH₃ | OCH₃ | |
| 6-CO₂CH₃ | O | H | H | H | CH₃ | SCH₃ | |
| 6-CO₂CH₃ | — | H | H | H | CH₃ | C₂H₅ | |
| 6-SO₂N(CH₃)₂ | O | H | H | H | CH₃ | CH₃ | |
| 6-SO₂N(CH₃)₂ | O | CH₃ | H | H | CH₃ | SCH₃ | |
| 2-SO₂N(CH₃)₂ | O | H | H | H | C₂H₅ | OC₂H₅ | |
| 6-OCH₂CH=CH₂ | — | H | H | H | CH₃ | SCH₃ | |
| 6-OCF₂H | — | H | 4'- | 2'- | CH₃ | SCH₃ | |

TABLE VI-continued

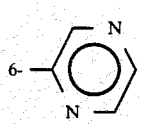

| R₁ | E | R | L₁ | L₂ | X₂ | Y₃ | m.p. (°C.) |
|---|---|---|---|---|---|---|---|
| 6-SC₂H₅ | O | H | 4'-Cl | Cl H | CH₃ | OCH₃ | |
| 6-SO₂CH₂CH₂CH₃ | — | H | H | H | CH₂CF₃ | CH₃ | |
| 2-SCH₃ | — | H | H | H | CH₃ | SCH₃ | |
| 6-(pyrimidinyl) | O | H | H | H | CH₃ | C₂H₅ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 15

| Wettable Powder | |
|---|---|
| 2-[[(4,6-dimethoxypyrimidin-2-yl)aminocarbonyl]aminosulfonyl]-4-phenylbenzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 16

| Wettable Powder | |
|---|---|
| 2-[[[(4-methoxy-6-methyl-1,3,5-triazin-2-yl)aminocarbonyl]aminosulfonyl]-4-phenylbenzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 17

| Granule | |
|---|---|
| Wettable Powder of Example 16 | 5% |
| attapulgite granules | 95% |
| (U.S.S. 20–40 mesh; 0.84–0.42 mm) | |

A slurry of wettable powder containing ≈25% solids is sprayed on the surface of attapulgite granules in a double-cone blender. The granules are dried and packaged.

EXAMPLE 18

| Extruded Pellet | |
|---|---|
| 2-[[(4,6-dimethoxypyrimidin-2-yl)aminocarbonyl]aminosulfonyl]-4-phenylbenzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

| Oil Suspension | |
|---|---|
| 2-[[(4-methoxy-6-methyl-1,3,5-triazin-2-yl)aminocarbonyl]aminosulfonyl]-4-phenylbenzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 20

| Wettable Powder | |
|---|---|
| 2-[[(4-methoxy-6-methyl-1,3,5-triazin-2-yl)aminocarbonyl]aminosulfonyl]-4-phenylbenzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 21

| Low Strength Granule | |
|---|---|
| 2-[[(4,6-dimethoxypyrimidin-2-yl)aminocarbonyl]aminosulfonyl]-4-phenylbenzoic acid, methyl ester | 1% |
| N,N—dimethylformamide | 9% |
| attapulgite granules | 90% |
| (U.S.S. 20–40 sieve) | |

The active ingredient is dissolved in the solvent and the solution is sprayed upon dedusted granules in a double cone blender. After spraying of the solution has been completed, the blender is allowed to run for a short period and then the granules are packaged.

EXAMPLE 22

| Aqueous Suspension | |
|---|---|
| 2-[[(4-methoxy-6-methyl-1,3,5-triazin-2-yl)aminocarbonyl]aminosulfonyl]-4-phenylbenzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 23

| Solution | |
|---|---|
| 2-[[(4,6-dimethoxypyrimidin-2-yl)aminocarbonyl]aminosulfonyl]-4-phenylbenzoic acid, methyl ester | 5% |
| water | 95% |

The salt is added directly to the water with stirring to produce the solution, which may then be packaged for use.

EXAMPLE 24

| Low Strenqth Granule | |
|---|---|
| 2-[[(4,6-dimethoxypyrimidin-2-yl)aminocarbonyl]aminosulfonyl]-4-phenylbenzoic acid, methyl ester | 0.1% |
| attapulgite granules | 99.9% |
| (U.S.S. 20–40 mesh) | |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 25

| Granule | |
|---|---|
| 2-[[(4-methoxy-6-methyl-1,3,5-triazin-2-yl)aminocarbonyl]aminosulfonyl]-4-phenylbenzoic acid, methyl ester | 80% |
| wetting agent | 1% |
| crude ligninsulfonate salt (containing 5–20% of the natural sugars) | 10% |

| Granule | |
|---|---|
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 26

| High Strength Concentrate | |
|---|---|
| 2-[[(4,6-dimethoxypyrimidin-2-yl)aminocarbonyl]aminosulfonyl]-4-phenylbenzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 27

| Wettable Powder | |
|---|---|
| 2-[[(4-methoxy-6-methyl-1,3,5-triazin-2-yl)aminocarbonyl]aminosulfonyl]-4-phenylbenzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 28

| Wettable Powder | |
|---|---|
| 2-[[(4,6-dimethoxypyrimidin-2-yl)aminocarbonyl]aminosulfonyl]-4-phenylbenzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 29

| Oil Suspension | |
|---|---|
| 2-[[(4-methoxy-6-methyl-1,3,5-triazin-2-yl)aminocarbonyl]aminosulfonyl]-4-phenylbenzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 30

| Dust | |
|---|---|
| 2-[[(4-methoxy-6-methyl-1,3,5-triazin-2-yl)aminocarbonyl]aminosulfonyl]-4-phenylbenzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

Test results indicate that the compounds of the present invention are active herbicides. They have utility for broad-spectrum pre- and/or or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, especially wheat, corn and rice.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types. They may also be used in combination with mefluidide.

The herbicidal properties of the subject compounds were discovered in a number of greenhouse tests. The test procedures and results follow.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea spp.), cocklebur (*Xanthium pensylvanicum*), sorghum, corn, soybean, cotton, sugar beet, rice, wheat and purple nutsedge (*Cyperus rotundus*) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
E=emergence inhibition;
G=growth retardation; and
H=formative effects.

The data show that several compounds from the scope of the invention provide selective control of weeds in crops such as wheat, corn and rice.

Compounds

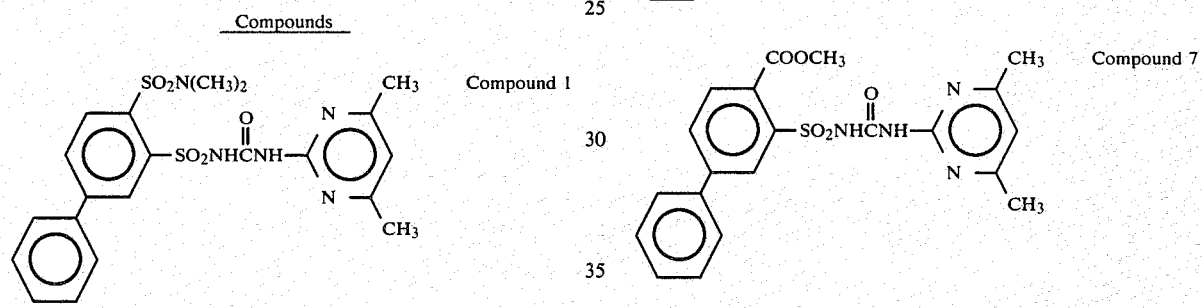

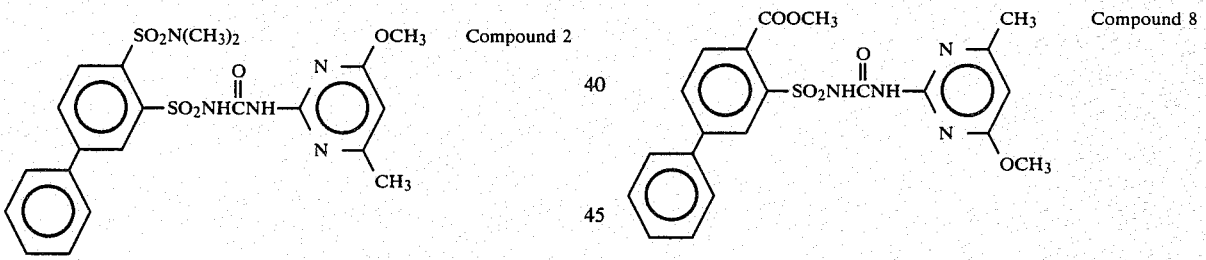

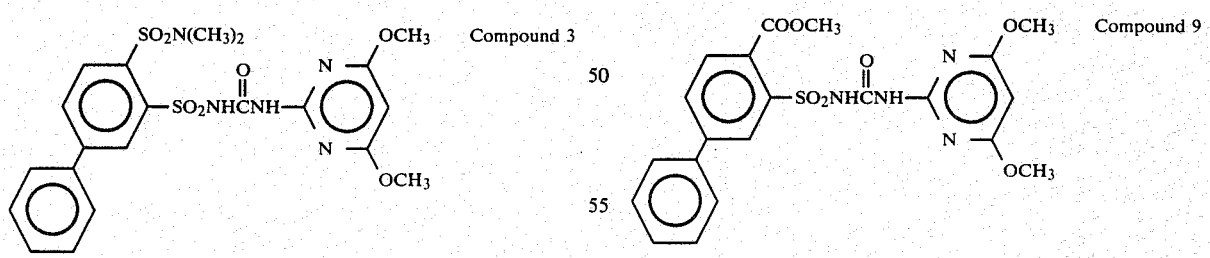

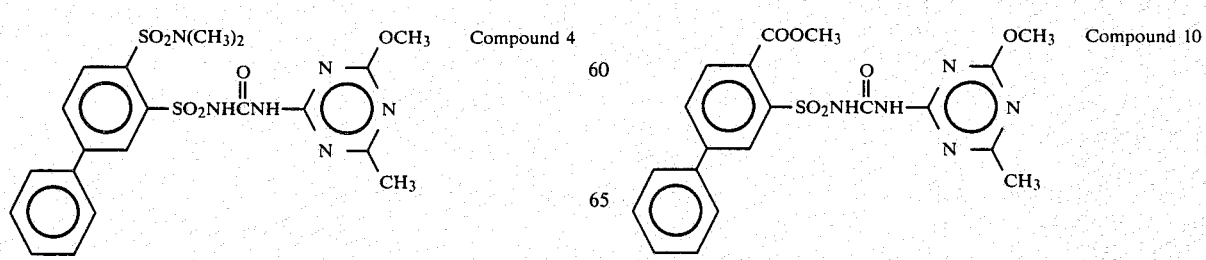

-continued
Compounds

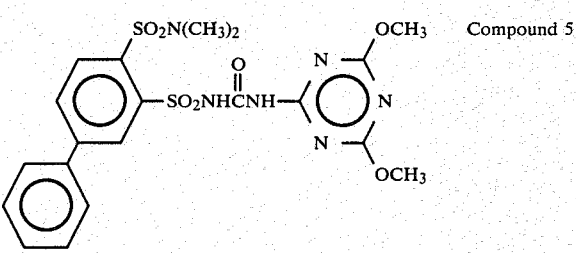

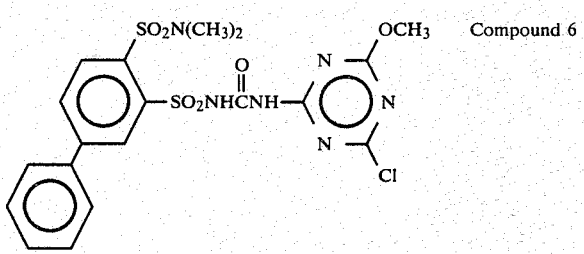

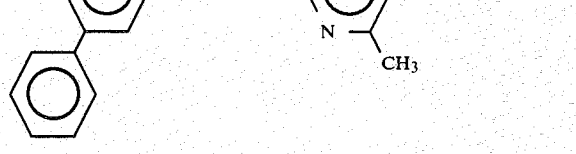

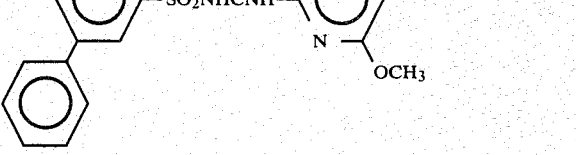

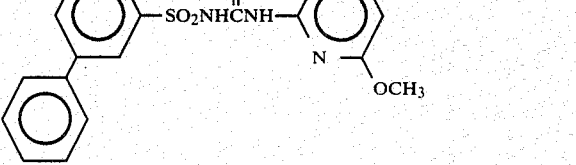

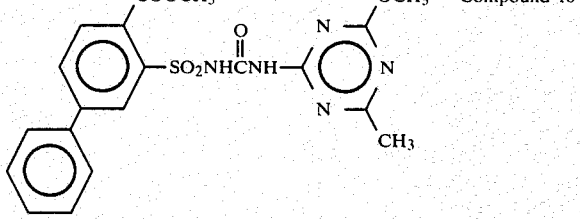

-continued
Compounds

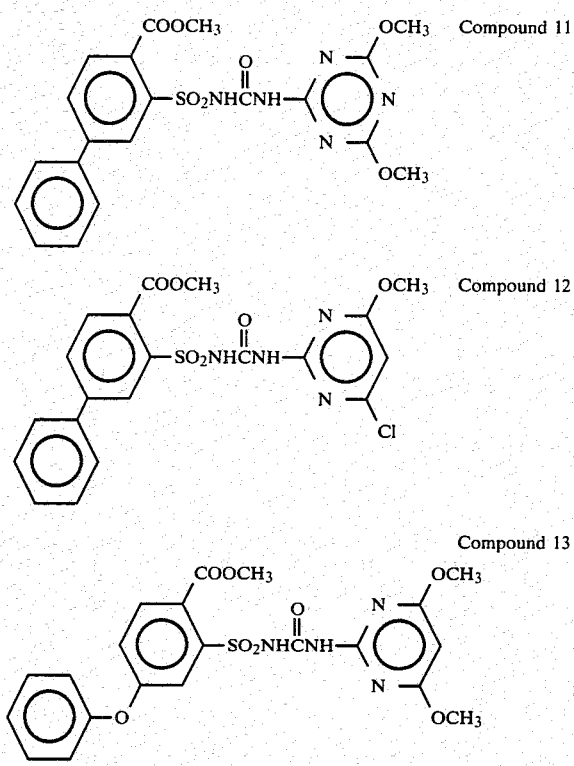

Compound 11

Compound 12

Compound 13

TEST B

Postemergence

Two round pans (25 cm diameter by 12.5 cm deep) were filled with Woodstown sandy loam soil. One pan was planted with blackgrass (*Alopercurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described for Test A.

Response ratings are contained in Table B. The data indicate again that several of the compounds tested have utility for weed control in corn, wheat and rice.

TABLE A

| Rate g/ha | Cmpd. 1 50 | Cmpd. 2 50 | Cmpd. 3 50 | Cmpd. 4 50 | Cmpd. 5 50 | Cmpd. 6 50 | Cmpd. 7 50 | Cmpd. 8 50 | Cmpd. 9 50 | Cmpd. 10 50 | Cmpd. 11 50 | Cmpd. 12 50 | Cmpd. 13 50 |
|---|---|---|---|---|---|---|---|---|---|---|---|---|---|
| POST-EMERGENCE | | | | | | | | | | | | | |
| Morningglory | 3C | 4C,5H | 3C,8G | 4C,9G | 6C,9G | 2C,4G | 2C,6G | 5C,9G | 3C,8H | 9C | 3C,9G | 3C,7G | 10C |
| Cocklebur | 2C | 2C,4G | 3C,8H | 5C,9G | 4C,9G | 2C,6G | 3C,9H | 3C,9H | 2C,8H | 9C | 5C,9G | 3C,9H | 6C,9H |
| Sicklepod | 2C | 2C,3G | 2C,7G | 4C,8G | 3C,8G | 2C,3G | 3C,9G | 5C,9G | 3C,9G | 4C,9G | 3C,9G | 2C | 2C,5G |
| Nutsedge | 2G | 0 | 0 | 8G | 0 | 3G | 2C,8G | 2C,9G | 2C,5G | 9C | 5C,9G | 2C,5G | 0 |
| Crabgrass | 0 | 0 | 2G | 0 | 0 | 0 | 0 | 1H | 0 | 2G | 0 | 0 | 3G |
| Barnyardgrass | 0 | 2C,3H | 2C | 3C,5H | 2C,3G | 2H | 3C,5H | 3C,9H | 1C | 2H | 0 | 0 | 5H |
| Wild Oats | 0 | 0 | 0 | 0 | 0 | 0 | 0 | 2C | 0 | 0 | 0 | 0 | 0 |
| Wheat | 0 | 0 | 0 | 0 | 0 | 0 | 0 | 0 | 0 | 0 | 0 | 0 | 0 |
| Corn | 0 | 0 | 2C,3G | 2H | 3G | 2G | 0 | 1C,4G | 2G | 2G | 0 | 0 | 2C,7H |
| Soybean | 3C,5H | 2C,9G | 3C,9G | 4C,9G | 5C,9G | 2C,2H | 3C,9G | 3C,9G | 2C,9G | 2C,9G | 4C,9G | 2C,5G | 3C,9G |
| Rice | 0 | 2C,3G | 2C,5G | 3G | 0 | 2C | 2G | 5G | 1H | 2C,9G | 3C,8H | 3G | 2G |
| Sorghum | 2G | 5G | 4G | 2C,7G | 5G | 2G | 9G | 2C,9H | 3G | 3H | 2C,7H | 0 | 3G |
| Sugar beet | 0 | 2C,5G | 4C,9G | 3C,8H | 3C,8H | 2C,4G | 9C | 4C,9H | 9C | 9C | 9C | 3C,8G | 3C,9G |
| Cotton | 2G | 2C,8G | 5C,9G | 10C | 5C,9G | 3C,5G | 2C,9G | 4C,9G | 5C,9G | 4C,9G | 4C,9G | 2C,7G | 4C,9G |
| PRE-EMERGENCE | | | | | | | | | | | | | |
| Morningglory | 0 | 3G | 1H | 3G | 5G | 0 | 0 | 2C,5G | 2C,8H | 9G | 9H | 0 | 9G |
| Cocklebur | — | — | 3H | — | — | 0 | 9H | 9H | 9H | 9H | 9H | — | 8H |
| SicklePod | 3G | 0 | 0 | 0 | 0 | 0 | 0 | 1C | 2C,5G | 3C,7H | 3G | 0 | 9G |
| Nutsedge | 0 | 0 | 0 | 0 | 0 | 0 | 0 | 3G | 0 | 4G | 0 | 0 | 0 |
| Crabgrass | 2G | 0 | 0 | 0 | 0 | 0 | 0 | 0 | 0 | 0 | 0 | 0 | 0 |
| Barnyardgrass | 2G | 2G | 0 | 0 | 0 | 0 | 2H | 3C,7G | 2C,4H | 1H | 0 | 0 | 2C,5G |
| Wild Oats | 0 | 2G | 0 | 0 | 0 | 0 | 0 | 3C,8G | 0 | 3C,8H | 2C,7G | 0 | 4G |
| Wheat | 0 | 0 | 0 | 0 | 0 | 0 | 0 | 2G | 0 | 0 | 0 | 0 | 2G |
| Corn | 0 | 2G | 0 | 0 | 0 | 0 | 4G | 2C,8H | 2C,4G | 3C,7G | 2C,3G | 0 | 2C,8G |
| Soybean | 0 | 0 | 0 | 0 | 7H | 0 | 0 | 1C | 1C,1H | 3C,6H | 3C,3H | 0 | 3C,6G |
| Rice | 2G | 2G | 0 | 3G | 4G | 0 | 2C,3G | 2C,8H | 2C,6G | 3C,8H | 4C,8H | 0 | 2C,5G |
| Sorghum | 0 | 3G | 0 | 0 | 2H | 0 | 2C,5H | 2C,8H | 6H | 2C,4G | 3C,4H | 0 | 5G |
| Sugar beet | 2G | 2G | 2G | 4G | 4G | 3G | 2C,7G | 9G | 8G | 9C | 10E | 6G | 8G |
| Cotton | 0 | 0 | 0 | 0 | 0 | 0 | 0 | 0 | 0 | 0 | 0 | 0 | 8G |

TABLE B

PRE-EMERGENCE ON WOODSTOWN SANDY LOAM

| | Compound 7 | | | Compound 8 | | | Compound 9 | | | Compound 10 | | | | Compound 11 | | | |
|---|---|---|---|---|---|---|---|---|---|---|---|---|---|---|---|---|---|
| Rate g/ha | 250 | 62 | 16 | 250 | 62 | 16 | 250 | 62 | 16 | 250 | 62 | 16 | 4 | 250 | 62 | 16 | 4 |
| POST-EMERGENCE | | | | | | | | | | | | | | | | | |
| Corn | 2G | 0 | 0 | 0 | 0 | 0 | 2G | 0 | 0 | 5G | 2G | 0 | 0 | 3G | 0 | 0 | 0 |
| Wheat | 0 | 0 | 0 | 0 | 0 | 0 | 0 | 0 | 0 | 2G | 0 | 0 | 0 | 2G | 0 | 0 | 0 |
| Rice | 0 | 0 | 0 | 2G | 0 | 0 | 0 | 0 | 0 | 8G | 5G | 2G | 0 | 9G | 5G | 3G | 0 |
| Soybean | 10G | 9G | 7G | 10G | 9G | 5G | 10G | 9G | 7G | 10G | 10G | 8G | 2G | 10G | 10G | 9G | 7G |
| Cotton | 8G | 8G | 2G | 10G | 8G | 3G | 10G | 8G | 5G | 10G | 10G | 6G | 2G | 9G | 6G | 2G | 0 |
| Sugar beet | 10G | 10G | 7G | 10G | 9G | 4G | 10G | 9G | 8G | 10G | 10G | 10G | 9G | 10G | 10G | 9G | 6G |
| Crabgrass | 0 | 0 | 0 | 0 | 0 | 0 | 2G | 0 | 0 | 0 | 0 | 0 | 0 | 0 | 0 | 0 | 0 |
| Johnsongrass | 2G | 0 | 0 | 2G | 0 | 0 | 0 | 0 | 0 | 2G | 0 | 0 | 0 | 4G | 2G | 0 | 0 |
| Blackgrass | 2G | 0 | 0 | 2G | 0 | 0 | 0 | 0 | 0 | 10G | 4G | 2G | 0 | 10G | 9G | 3G | 0 |
| Barnyardgrass | 2G | 0 | 0 | 0 | 0 | 0 | 0 | 0 | 0 | 2G | 0 | 0 | 0 | 2G | 0 | 0 | 0 |
| Nutsedge | 4G | 2G | 0 | 7G | 4G | 2G | 3G | — | — | 10G | 9G | 5G | 2G | 5G | 3G | 2G | — |
| Giant Foxtail | 2G | 0 | 0 | 0 | 0 | 0 | 0 | 0 | 0 | 3G | 0 | 0 | 0 | 3G | 0 | 0 | 0 |
| Wild Oats | 0 | 0 | 0 | 2G | 0 | 0 | 0 | 0 | 0 | 3G | 0 | 0 | 0 | 3G | 0 | 0 | 0 |
| Cocklebur | 9G | 8G | 6G | 10G | 9G | 6G | 10G | 9G | 6G | 10G | 10G | 10G | 10G | 10G | 10G | 9G | 6G |
| Morningglory | 10G | 4G | 2G | 10G | 7G | 3G | 10G | 10G | 4G | 10G | 10G | 10G | 8G | 10G | 10G | 8G | 5G |
| Teaweed | 3G | 0 | 0 | 4G | 2G | 0 | 8G | 4G | 2G | 7G | 4G | 2G | 0 | 8G | 4G | 2G | 0 |
| SicklePod | 6G | 3G | 0 | 8G | 3G | 0 | 8G | 5G | 2G | 10G | 7G | 3G | 0 | 9G | 5G | 2G | 2G |
| Jimsonweed | 6G | 4G | 2G | 9G | 8G | 5G | 9G | 8G | 6G | 9G | 9G | 6G | 2G | 9G | 6G | 2G | 0 |
| Velvetleaf | 9G | 8G | 5G | 10G | 9G | 5G | 10G | 10G | 7G | 10G | 10G | 6G | 4G | 10G | 10G | 8G | 3G |
| PRE-EMERGENCE | | | | | | | | | | | | | | | | | |
| Corn | 0 | 0 | | 0 | 0 | | 0 | 0 | | 2G | 0 | | | 2G | 0 | | |
| Wheat | 0 | 0 | | 0 | 0 | | 0 | 0 | | 0 | 0 | | | 0 | 0 | | |
| Rice | 6G | 2G | | 5G | 0 | | 4G | 0 | | 9G | 6G | | | 9G | 6G | | |
| Soybean | 2G | 0 | | 2G | 0 | | 0 | 0 | | 7G | 4G | | | 5G | 2G | | |
| Cotton | 2G | 0 | | 2G | 0 | | 0 | 0 | | 4G | 0 | | | 2G | 0 | | |
| Sugar beet | 7G | 2G | | 7G | 2G | | 7G | 5G | | 9G | 9G | | | 9G | 8G | | |
| Crabgrass | 2G | 0 | | 4G | 2G | | 2G | 0 | | 4G | 2G | | | 2G | 0 | | |
| Johnsongrass | 7G | 4G | | 6G | 2G | | 2G | 0 | | 4G | 0 | | | 5G | 3G | | |
| Blackgrass | 6G | 3G | | 8G | 6G | | 9G | 3G | | 9G | 8G | | | 9G | 5G | | |
| Barnyardgrass | 6G | 3G | | 5G | 0 | | 2G | 0 | | 3G | 0 | | | 4G | 0 | | |
| Nutsedge | 4G | 0 | | 4G | 0 | | 3G | 0 | | 6G | 4G | | | 2G | 0 | | |
| Giant Foxtail | 7G | 4G | | 6G | 0 | | 0 | 0 | | 3G | 0 | | | 4G | 0 | | |
| Wild Oats | 0 | 0 | | 0 | 0 | | 0 | 0 | | 0 | 0 | | | 0 | 0 | | |
| Cocklebur | 7G | 2G | | 7G | 4G | | 4G | 2G | | 9G | 7G | | | 10G | 7G | | |
| Morningglory | 0 | 0 | | 3G | 0 | | 3G | 0 | | 8G | 4G | | | 8G | 3G | | |
| Teaweed | 5G | 2G | | 8G | 2G | | 5G | 2G | | 8G | 4G | | | 6G | 3G | | |
| SicklePod | 8G | 3G | | 6G | 3G | | 4G | 0 | | 6G | 2G | | | 3G | 0 | | |
| Jimsonweed | 6G | 3G | | 10G | 6G | | 10G | 4G | | 10G | 7G | | | 8G | 3G | | |
| Velvetleaf | 3G | 0 | | 9G | 5G | | 4G | 0 | | 9G | 7G | | | 7G | 0 | | |

What is claimed is:

1. A compound of the formula

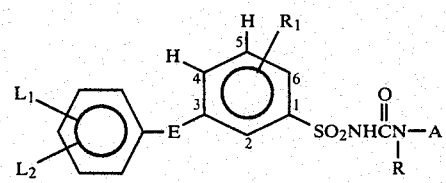

wherein
E is O or a single bond;
$L_1$ is H, F, Cl, Br, $NO_2$, $CH_3$, $OCH_3$ or $CF_3$;
$L_2$ is H, F, Cl, Br, $CH_3$ or $OCH_3$;
R is H or $CH_3$;
$R_1$ is $CO_2R_2$, $S(O)_nR_3$, $SO_2NR_4R_5$, $SO_2N(OCH_3)CH_3$, $OSO_2R_6$, $WCF_3$, $WCHF_2$, $C_3$-$C_4$ alkenyloxy, $C_3$-$C_4$ alkynyloxy, $C_1$-$C_2$ alkyl substituted with $OCH_3$ or $OC_2H_5$, $CH_2CH_2Cl$, $CF_3$,

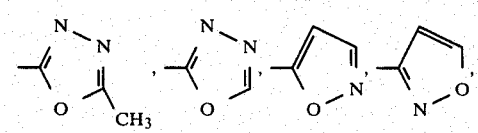

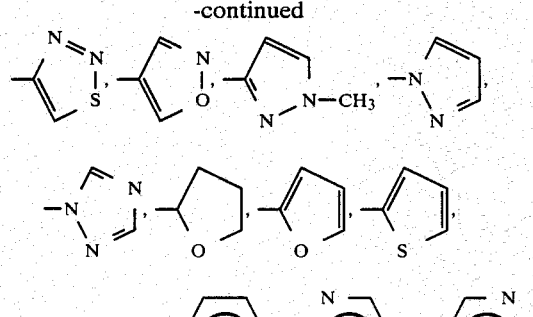

$R_2$ is $C_1$-$C_3$ alkyl, $CH_2CH=CH_2$, $CH_2CH_2OCH_3$ or $CH_2CH_2Cl$;
$R_3$ is $C_1$-$C_3$ alkyl or $CH_2CH=CH_2$;
$R_4$ is H or $C_1$-$C_2$ alkyl;
$R_5$ is $C_1$-$C_2$ alkyl;
$R_6$ is $C_1$-$C_3$ alkyl, $CF_3$ or $N(CH_3)_2$;
W is O or S;
n is 0, 1 or 2;
A is

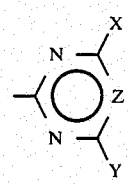

X is $CH_3$, $OCH_3$, $OCH_2CH_3$, $OCF_2H$, $CH_2F$, $CH_2Cl$, $CH_2Br$ or $CF_3$;

Y is H, $CH_3$, $OCH_3$, $OCH_2CH_3$, $CH_2OCH_3$, $CH_2OCH_2CH_3$, $NH_2$, $NHCH_3$, $N(CH_3)_2$, $N(OCH_3)CH_3$, $CH_2CH_3$, $CF_3$, $SCH_3$, $OCH_2CH=CH_2$, $OCH_2C\equiv CH$, $OCH_2CF_3$, $OCH_2CH_2OCH_3$, $CH_2SCH_3$, $OCF_2H$, $OCH_2CH_2F$, $-CH(OCH_3)_2$,

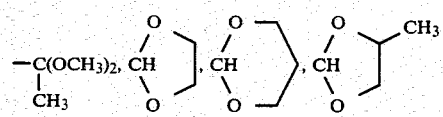

$CH(OCH_2CH_3)_2$ or

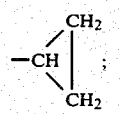

Z is N.

2. A compound of claim 1 where $R_1$ is in the 6-position and R is H.

3. A compound of claim 2 where Y is $CH_3$, $C_2H_5$, $OCH_3$, $OC_2H_5$, $CH_2OCH_3$, $CH_2OC_2H_5$, $CF_3$, $OCH_2CF_3$ or $CH(OCH_3)_2$.

4. A compound of claim 3 where $L_2$ is H, $R_1$ is $CO_2R_2$, $SO_2R_3$, $SO_2NR_4R_5$ or $SO_2N(OCH_3)CH_3$ and $R_4$ is $C_1$-$C_2$ alkyl.

5. A compound of claim 4 where $L_1$ is H, Cl or $CH_3$, X is $CH_3$ or $OCH_3$ and Y is $CH_3$, $C_2H_5$, $OCH_3$, $OC_2H_5$ or $CH_2OCH_3$.

6. A compound of claim 5 wherein E is a single bond and $L_1$ is H.

7. The compound of claim 1 which is 2-[[(4-methoxy-6-methyl-1,3,5-triazin-2-yl)aminocarbonyl]aminosulfonyl]-4-phenylbenzoic acid, methyl ester.

8. A composition suitable for controlling the growth of undesired vegetation which comprises an effective amount of a compound of claim 1 and at least one of the following: surfactant, solid or liquid inert diluent.

9. A composition suitable for controlling the growth of undesired vegetation which comprises an effective amount of a compound of claim 2 and at least one of the following: surfactant, solid or liquid inert diluent.

10. A composition suitable for controlling the growth of undesired vegetation which comprises an effective amount of a compound of claim 3 and at least one of the following: surfactant, solid or liquid inert diluent.

11. A composition suitable for controlling the growth of undesired vegetation which comprises an effective amount of a compound of claim 4 and at least one of the following: surfactant, solid or liquid inert diluent.

12. A composition suitable for controlling the growth of undesired vegetation which comprises an effective amount of a compound of claim 5 and at least one of the following: surfactant, solid or liquid inert diluent.

13. A composition suitable for controlling the growth of undesired vegetation which comprises an effective amount of a compound of claim 6 and at least one of the following: surfactant, solid or liquid inert diluent.

14. A method for controlling the growth of undesired vegetation which comprises applying to the locus to be protected an effective amount of a compound of claim 1.

15. A method for controlling the growth of undesired vegetation which comprises applying to the locus to be protected an effective amount of a compound of claim 2.

16. A method for controlling the growth of undesired vegetation which comprises applying to the locus to be protected an effective amount of a compound of claim 3.

17. A method for controlling the growth of undesired vegetation which comprises applying to the locus to be protected an effective amount of a compound of claim 4.

18. A method for controlling the growth of undesired vegetation which comprises applying to the locus to be protected an effective amount of a compound of claim 5.

19. A method for controlling the growth of undesired vegetation which comprises applying to the locus to be protected an effective amount of a compound of claim 6.

* * * * *